(12) United States Patent
Probasco

(10) Patent No.: US 8,142,820 B2
(45) Date of Patent: Mar. 27, 2012

(54) METHODS FOR TREATING OR PREVENTING INFESTATION

(75) Inventor: Gene Probasco, Yakima, WA (US)

(73) Assignee: John L. Hass, Inc., Washington, DC (US)

( * ) Notice: Subject to any disclaimer, the term of this patent is extended or adjusted under 35 U.S.C. 154(b) by 188 days.

(21) Appl. No.: 12/311,259

(22) PCT Filed: Sep. 21, 2007

(86) PCT No.: PCT/US2007/020441
§ 371 (c)(1),
(2), (4) Date: Sep. 9, 2009

(87) PCT Pub. No.: WO2008/039362
PCT Pub. Date: Apr. 3, 2008

(65) Prior Publication Data
US 2010/0024071 A1 Jan. 28, 2010

Related U.S. Application Data

(60) Provisional application No. 60/847,203, filed on Sep. 25, 2006.

(51) Int. Cl.
*A01N 65/00* (2009.01)
(52) U.S. Cl. ..................................................... 424/725
(58) Field of Classification Search ........................ None
See application file for complete search history.

(56) References Cited

U.S. PATENT DOCUMENTS

| | | | |
|---|---|---|---|
| 3,615,660 A | 10/1971 | Bavisotto et al. |
| 3,866,171 A | 2/1975 | Parsons |
| 4,148,873 A | 4/1979 | Owades |
| 4,170,638 A | 10/1979 | Owades |
| 5,227,162 A | 7/1993 | Ferrari |
| 5,372,817 A | 12/1994 | Locke et al. |
| 5,827,895 A | 10/1998 | Nutter et al. |
| 6,096,350 A | 8/2000 | Kemp et al. |
| 6,204,283 B1 | 3/2001 | Black et al. |
| 6,379,720 B1 | 4/2002 | Cooper et al. |
| 6,646,014 B2 | 11/2003 | Watkins |
| 6,702,645 B2 | 3/2004 | Vanderpool |
| 7,597,912 B2 | 10/2009 | Probasco |
| 2001/0014346 A1 | 8/2001 | Watkins |
| 2002/0051804 A1 | 5/2002 | Probasco et al. |
| 2003/0060379 A1 | 3/2003 | Souter et al. |
| 2003/0129270 A1 | 7/2003 | Probasco |
| 2004/0091558 A1 | 5/2004 | Lutz et al. |
| 2005/0043404 A1 | 2/2005 | Probasco et al. |
| 2005/0049230 A1 | 3/2005 | Henrich et al. |
| 2005/0220914 A1 | 10/2005 | Probasco et al. |
| 2006/0009122 A1 | 1/2006 | Swanson |
| 2006/0013870 A1 | 1/2006 | Kuhrts |
| 2009/0005322 A1 * | 1/2009 | Purpura et al. .................. 514/21 |

FOREIGN PATENT DOCUMENTS

| | | |
|---|---|---|
| GB | 2330076 A | 4/1999 |
| JP | 05170525 A | 7/1993 |
| WO | WO-2007120461 A2 | 10/2007 |

OTHER PUBLICATIONS

Jones et al., "Repellant and Oviposition-Detering Effects of Hop-Beta Acids on the Two-Spotted Spider Mite Tetranychus Urticae," Pesticide Science, vol. 47, No. 2, pp. 165-169 (1996).
Caplus Online Abstract Accession No. 1997: 673259; Sakai, Shigeo, "Mild antimicrobial materials in foods", Shoku no Kagaku (1997), 235, 82-90.
"Culpeper's Complete Herbal A book of Natural Remedies for Acient Ills"Wordsworth Reference, pp. 134-135(1995).
Engelson et al. "Antimycotic properties of hop extract in reduced water activity media" Journal of Food Science (1980), 5(5), 1175-8.
Jones, G., "Potential Control of Two-Spotted Spider Mite, Tetranychua Urticae Koch, Using Hop b-Fraction," (1998) pp. 1-165, A thesis submitted for the degree of Doctor of Philosoph of the Universtiy of London and for the Diploma of Imperial College of Science, Technology & Medicine.
Losel et al., The Potential of Semidochemicals for Control of Phorodon Hummuli (Homoptera:Aphididae), Pesticide Science, vol. 48, No. 4, pp. 293-303 (1996).
WPI Online Abstract Accession No. 1978-32609A:JP53-029925 A (AJINOMOTO KK) Mar. 20, 1978.

* cited by examiner

*Primary Examiner* — Michael Meller
(74) *Attorney, Agent, or Firm* — Edwards Wildman Palmer LLP; Jeffrey D. Hsi; Melissa Hunter-Ensor, Esq.

(57) ABSTRACT

The present invention provides methods and compositions for controlling a fungal or insect infestation.

2 Claims, 17 Drawing Sheets

Marketable Fruit. This graph illustrates the number of marketable fruit per plot harvested.

US 8,142,820 B2
                                                        1                                                                  2
            METHODS FOR TREATING OR                                       Sphaerotheca (e.g., Sphaerotheca fuliginea or Sphaerotheca
             PREVENTING INFESTATION                                       macularis),    Rasutoria    (e.g.,   Rasutoria    abietis),
                                                                          Microsphaera    (e.g.,    Microsphaera    penicillata    or
              CROSS REFERENCE TO RELATED                                  Microsphaera alphitoides), Podosphaera e.g., Podosphaera
                    APPLICATIONS                                          spp. Kunze), Peronospora (Peronospora parasitica), Phy-
                                                                          tophthora (e.g., Phytophthora infestans), Pseudoperono-
           This application is the National Stage of PCT/US2007/          spora (e.g., Pseudoperonospora cubensis), and Plasmopara
        020441, filed Sep. 21, 2007, which is a continuation-in-part      (e.g., Plasmopara viticola) with an effective amount of a
        of U.S. provisional application Ser. No. 60/847,203, filed        composition comprising a hop derivative, thereby controlling
        Sep. 25, 2006, and which is incorporated herein by reference      the fungus. In other embodiments, the fungus infects any one
        in its entirety.                                                  or more of the following crop plants: asparagus, bean, beet,
                                                                          carrot, celery, chicory, crucifers, cucurbits, eggplant, endive,
              BACKGROUND OF THE INVENTION                                 grape, lettuce, onion, pepper, potato, raspberry, rhubarb, ruta-
                                                                          baga, shallot, strawberry, tomato, and turnip. In another
           Many plants are susceptible to disease caused by a variety     embodiment, the fungus infects an ornamental plant selected
        of pests, including fungi and insects. Such pests seriously       from the group consisting of anemone, begonia, calendula,
        damage a crop and reduce its economic value to the grower.        chrysanthemum, dahlia, dogwood, fuchsia, geranium, haw-
        Crop plants are particularly vulnerable, and when disease         thorn, heather, hydrangea, marigold, pansy, peony, peri-
        strikes, losses can be severe. Many conventional insecticides     winkle, petunia, rose, snapdragon, sunflower, sweet peat,
        and fungicides have detrimental effects on the environment        tulip, violet, and zinnia.
        and are implicated in human toxicity. Present methods of             In yet another aspect, the invention features a method of
        controlling or preventing insects and fungal disease of crop      treating or preventing a plant fungal or insect infestation, the
        plants are unsatisfactory. A need therefore exists for new        method comprising contacting a plant, plant growth material
        methods of protecting plants from insects and fungal disease.     (e.g., soil, vermiculite, compost), or plant container (e.g., pot
                                                                          or tray) with an effective amount of a composition comprising
                SUMMARY OF THE INVENTION                                  a hop derivative, thereby treating or preventing a plant fungal
                                                                          or insect infestation. In one embodiment, the contacting
           As described below, the present invention features compo-     occurs in a field, green house, or home.
        sitions comprising hop acids and methods for reducing or             In yet another aspect, the invention provides a composition
        preventing a plant infestation.                                   for treating or preventing a fungal or insect larval infestation,
           In one aspect, the invention provides a method of control-    the composition comprising an effective amount of a hop
        ling an insect (e.g., Lepidoptera larva), the method compris-     derivative in an agriculturally suitable vehicle. In one
        ing contacting a plant or the insect with an effective amount of  embodiment, the hop derivative is an alpha acid, beta acid, or
        a composition comprising a hop derivative, thereby control-       combination of alpha and beta acids. In another embodiment,
        ling the insect. In one embodiment, the contacting occurs         the composition is any one or more of a liquid, a powder, a
        while the insect is in contact with the plant (e.g., a solana-    colloid, an oil, and an emulsion. In yet another embodiment,
        ceous plant, such as tomato, tomatillo, pepper, chili, potato,    the composition further comprises a surfactant, such as a
        and eggplant or a cruciferous plant, such as broccoli, Brussels   soap.
        sprouts, cabbage, cauliflower, collard greens, kale, kohlrabi,       In yet another aspect, the invention provides an insecticide
        mustard, rutabaga, turnips, bok choy, Chinese cabbage Aru-        or fungicide delivery device (e.g., a spray gun, high volume
        gula, horse radish, radish, wasabi and watercress. In another     field sprayer, aerosol spray canister, mister) comprising the
        embodiment, the insect is any one or more of cabbage loop-        composition of previous aspect
        ers, diamondback moth larvae, alfalfa looper, armyworm,              In still another aspect, the invention provides a plant com-
        beet armyworm, artichoke plume moth, cabbage budworm,             prising a composition of any previous aspect.
        cabbage looper, cabbage webworm, corn earworm, celery                In still another aspect, the invention provides a method of
        leafeater, cross-striped cabbageworm, european corn borer,        making the composition of any previous aspect.
        green cloverworm, imported cabbageworm, melonworm,                   In yet another aspect, the invention provides a kit for the
        omnivorous leafroller, pickleworm, rindworm complex, salt-        treatment or prevention of an insect larva or fungal infesta-
        marsh caterpillar, soybean looper, tobacco budworm, tomato        tion, the kit comprising an effective amount of a hop deriva-
        fruitworm, tomato hornworm, tomato pinworm, velvetbean            tive in a form suitable for delivery to a site of infestation. In
        caterpillar, yellowstriped armyworm, apple tortrix moth, fruit    one embodiment, the site of infestation is a plant, plant
        tree tortrix moth, apple fruit moth, silvery moth, apple pith     growth material, plant container, or greenhouse.
        moth, cactus moth, spotted stalk borer, tomato looper, tortrix       In still another aspect, the invention provides a method of
        moth, crownvetch casebearer moth, red clover casebearer           identifying a hop derivative that controls an insect. The
        moth, clover case-bearer moth, leek moth, leaf worm, noctuid      method involves contacting the insect or insect larva with a
        moth, Nut fruit tortrix, chestnut tortrix, Siberian silk moth,    test composition comprising a hop derivative; and identifying
        pumpkin caterpillar, cherry bark tortrix, stem borer, oriental    a hop derivative that reduces a larva biological function rela-
        fruit moth, opean poplar shoot borer, old world bollworm,         tive to an untreated insect or larva. In various embodiments,
        cotton bollworm, gypsy moth, cabbage moth, bean pod borer,        the test compound kills the insect or insect larva, reduces
        large yellow underwig, leaf roller, Pink bollworm, Egyptian       larval hatching, growth, or feeding, or repels the insect or
        cottonworm, false codling moth, and apple ermine moth.            insect larva.
           In another aspect, the invention provides a method of con-        In yet another aspect, the invention features a method of
        trolling a fungus, the method comprising contacting a fungus      identifying a hop derivative that controls a fungus. The
        or spore that is any one or more of Botrytis (Botrytis cinerea,   method involves contacting the fungus with a test composi-
        Botrytis paeoniae, Botrytis tulipae), Erysiphe (e.g., E. cicho-   tion comprising a hop derivative; and identifying a hop
        racearum, E. cruciferarum, E. lycopersici, E. necator, E. pisi,   derivative that reduces fungal growth or survival relative to an
        and E. heraclei), Leveillula (e.g., Leveillula taurica),          untreated fungus. In another embodiment, the test compound reduces fungus growth or transmission. In yet another embodiment, the test compound reduces plant damage or increases marketable fruit yield.

In yet another aspect, the invention features a method of identifying a hop derivative that repels an insect. The method involves contacting a plant with a test composition comprising a hop derivative; contacting the plant with an insect; and assaying the amount of time the insect spend in contact with or feeding on the plant relative to an untreated plant, wherein a reduction in the amount of time in contact with or feeding on the treated plant identifies the hop derivative as repelling the insect.

In various embodiments of any of the above aspects, the composition reduces an infestation with an insect that is any one or more of a cabbage looper, diamondback moth larva, alfalfa looper, armyworm, beet armyworm, artichoke plume moth, cabbage budworm, cabbage looper, cabbage webworm, corn earworm, celery leafeater, cross-striped cabbageworm, european corn borer, green cloverworm, imported cabbageworm, melonworm, omnivorous leafroller, pickleworm, rindworm complex, saltmarsh caterpillar, soybean looper, tobacco budworm, tomato fruitworm, tomato hornworm, tomato pinworm, velvetbean caterpillar, yellowstriped armyworm, apple tortrix moth, fruit tree tortrix moth, apple fruit moth, silvery moth, apple pith moth, cactus moth, spotted stalk borer, tomato looper, tortrix moth, crownvetch casebearer moth, red clover casebearer moth, clover case-bearer moth, leek moth, leaf worm, noctuid moth, Nut fruit tortrix, chestnut tortrix, Siberian silk moth, pumpkin caterpillar, cherry bark tortrix, stem borer, oriental fruit moth, open poplar shoot borer, old world bollworm, cotton bollworm, gypsy moth, cabbage moth, bean pod borer, large yellow underwig, leaf roller, Pink bollworm, Egyptian cottonworm, false codling moth, and apple ermine moth. In still other embodiment reduces an infestation with a fungus or spore that is any one or more of a *Botrytis*, *Erysiphe*, *Leveillula*, *Sphaerotheca*, *Rasutoria*, *Microsphaera*, *Podosphaera*, *Peronospora*, *Pseudoperonospora*, and *Plasmopara*. In other embodiments of any of the above aspects, the invention provides a method of controlling a fungus, the method comprising contacting a fungus or spore that is any one or more of *Botrytis* (*Botrytis cinerea*, *Botrytis paeoniae*, *Botrytis tulipae*), *Erysiphe* (e.g., *E. cichoracearum*, *E. cruciferarum*, *E. lycopersici*, *E. necator*, *E. pisi*, and *E. heraclei*), *Leveillula* (e.g., *Leveillula taurica*), *Sphaerotheca* (e.g., *Sphaerotheca fuliginea* or *Sphaerotheca macularis*), *Rasutoria* (e.g., *Rasutoria abietis*), *Microsphaera* (e.g., *Microsphaera penicillata* or *Microsphaera alphitoides*), *Podosphaera* e.g., *Podosphaera* spp. Kunze), *Peronospora* (*Peronospora parasitica*), *Phytophthora* (e.g., *Phytophthora infestans*), *Pseudoperonospora* (e.g., *Pseudoperonospora cubensis*), and *Plasmopara* (e.g., *Plasmopara viticola*) with an effective amount of a composition comprising a hop derivative, thereby controlling the fungus. In other embodiments of the above aspects, the hop derivative is an isolated alpha acid, beta acid, or combination of an alpha and a beta acid. In still other embodiments of the above aspects, the composition contains 0.1%, 0.25%, 0.5%, 1%, 5%, 10%, 20%, 25%, 50%, 75% or more alpha acids, beta acids or a combination thereof.

Other features and advantages of the invention will be apparent from the detailed description, and from the claims.

Definitions

By "insecticide" is meant any agent, compound, or molecule that slows, delays, inhibits, or arrests the hatching, growth, viability, molting, or reproduction of an insect larva by at least 5%, 10%, 20%, 30%, 40%, 50%, 60%, or even by as much as 70%, 80%, 90%, 95%, or 99%.

By an "isolated hop derivative" is meant a hop component (e.g., alpha or beta acid) that has been separated from components that naturally accompany it. Typically, the hop derivative is isolated when it is at least 60%, by weight, free from the proteins and naturally-occurring organic molecules with which it is naturally associated. Preferably, the preparation is at least 75%, more preferably at least 90%, and most preferably at least 99%, by weight, a composition of the invention. An isolated hop derivative of the invention may be obtained, for example, by extraction from a natural source or by chemically synthesizing the derivative. Purity can be measured by any appropriate method, for example, column chromatography, polyacrylamide gel electrophoresis, or by HPLC analysis.

By "agricultural vehicle" is meant a plant-compatible excipient. Such vehicles lack or have reduced phytotoxicity.

By "alpha acid" is meant an organic acid derived from a hop plant (*Humulus lupulus*) having structural homology to humulone, adhumulone, cohumulone, or an analog or derivative thereof. Humulone, adhumulone, and cohumulone are the three most abundant alpha acid analogs. Other exemplary derivatives of an alpha acid include, but are not limited to isoalpha acids, rhoisoalpha acids, tetrahydroisoalpha acids, and hexahydroisoalpha acids.

By "beta acid" is meant an organic acid derived from a hop plant (*Humulus lupulus*) having structural homology to lupulone, adlupulone, colupulone or an analog or derivative thereof. Lupulone, adlupulone, and colupulone are the three most abundant beta acid analogs. Other exemplary derivatives of a beta acid include, but are not limited to, hulupones, hexahydrobeta acids and hexahydrohulupones.

By "biological function" is meant any physiological or behavioral activity of an organism.

By "contacting" is meant touching, associating with, or having proximity to a composition. For example, a hop derivative may contact a hive either inside or outside of the hive structure.

By "repels an insect" is meant reduces the amount of time an insect spends in contact with, feeding on, or in proximity with a treated plant relative to an untreated plant (e.g., a control plant). For example, a repellant reduces the amount of time that an insect spends within an area treated with a composition of the invention.

By "controlled release" is meant released over the course of hours, days, weeks, or months.

By "controlling an insect larva" is meant inhibiting insect larva (e.g., *Lepidoptera*) survival or reducing, slowing, or stabilizing the growth of an insect population. Preferably, survival is reduced by at least 5%, 10%, 20% or 25%, more preferably by 30%, 50%, 75%, 85% or even by as much as 95% or 100%.

By "controlling a fungus" is meant inhibiting fingal survival or reducing, slowing, or stabilizing the growth of a fungus. Preferably, a fungus is reduced by at least 5%, 10%, 20% or 25%, more preferably by 30%, 50%, 75%, 85% or even by as much as 95% or 100%.

By "insect damage is meant any damage to a plant tissue related to insect activity.

By "effective amount of an insecticide" is meant an amount effective to disrupt an insect biological fimction.

By "effective amount of a fungicide" is meant an amount effective to prevent, reduce, or slow the growth or proliferation of a fingus.

By "hop acids" is meant alpha or beta acids.

By "hop derivative" is meant any molecule that naturally occurs in hops (Humulus lupulus) and chemical derivatives thereof. Hop derivatives (e.g., alpha acids, beta acids) may be purified from hops or may be chemically synthesized.

By "infestation" is meant the colonization of a site or the consumption of a plant by a pest (e.g., insect or plant pathogen, such as a fungus). In preferred embodiments, infestation is reduced by at least 20% (and preferably 30% or 40%) relative to a control plant. In other preferred embodiments, infestation is reduced by 50%, 60%, and more preferably even 75% or 90% or more, up to 100% as compared to a control plant. The level of infestation is measured using conventional means that are known to the skilled artisan and described herein. For example, the level of infestation may be determined by comparing physical features and characteristics (for example, the amount of marketable fruit, plant height and weight, or by comparing symptoms of infestation, for example, lesion development, lesion size, leaf wilting and curling, water-soaked spots, amount of insect or fingal growth, evidence of insect feeding, number of insects or their eggs, presence of fungus, and discoloration of cells).

By "insecticidal activity" is meant any activity that inhibits the growth, reproduction, or survival of an insect.

By "fungicidal activity" is meant any activity that inhibits the growth, reproduction, or survival of a fungus.

By "preventing a pest infestation" is meant reducing the probability that an infestation will be established in a plant.

By "treating a plant infestation" is meant reducing, stabilizing, or slowing the growth of a insect or fungus in a plant.

By "plant pathogen" is meant an organism whose infection of viable plant tissue elicits a disease response in the plant tissue.

DETAILED DESCRIPTION OF THE INVENTION

Figure 1:
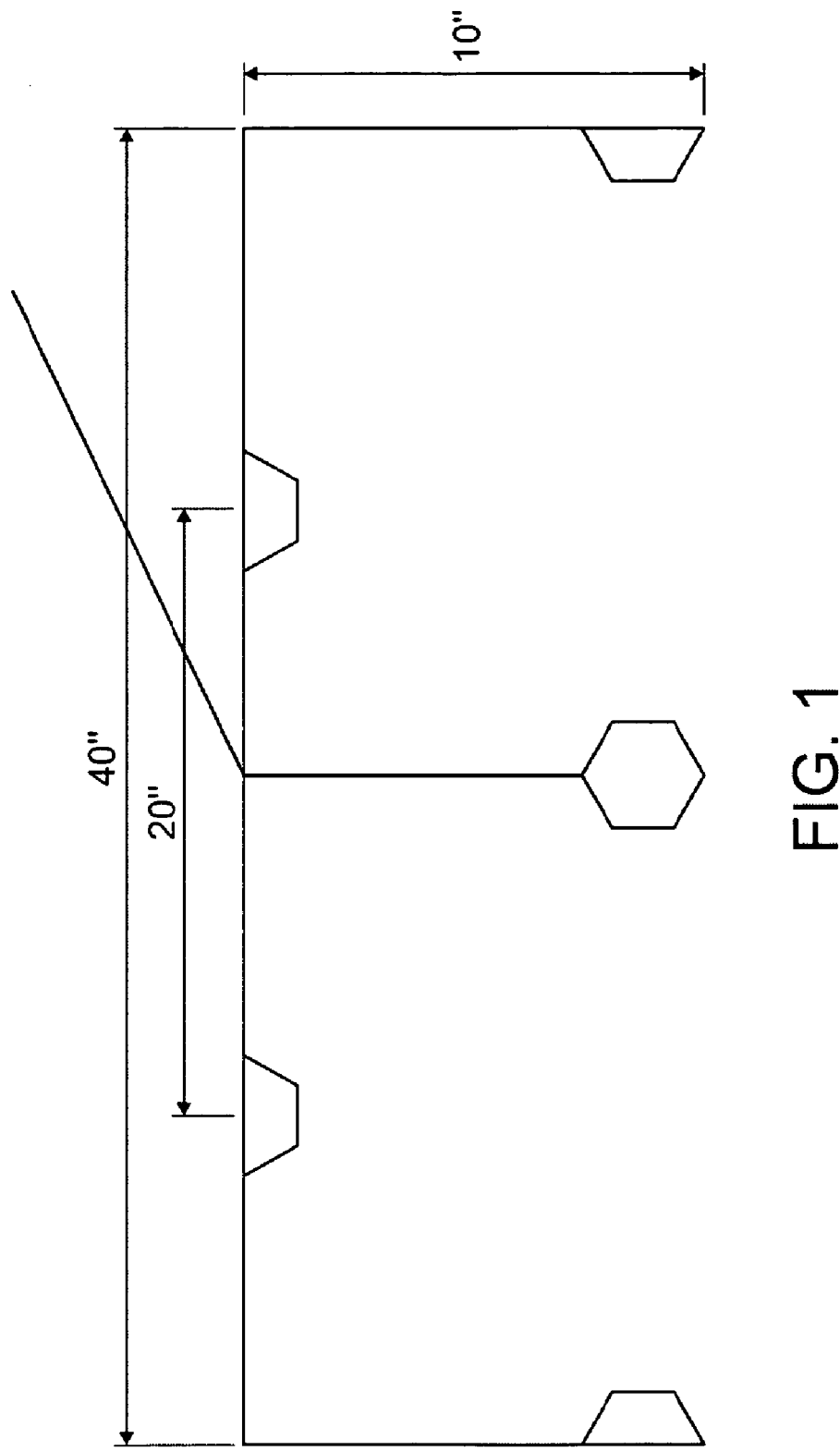
FIG. 1 is a schematic diagram of a boom sprayer. Boom sprayers meter the pesticide solution out of several nozzles (illustrated as quadrangles) along a long pipe or other structure called a boom.

As described below, the present invention features insecticide and fungicide compositions comprising hop acids and their derivatives and methods for reducing or preventing the infection or infestation of a plant with an insect or fungus. The invention is based, in part, on the discovery that naturally occurring components of hops are useful for the prevention or treatment of plant fungal diseases, such as *Botrytis*, powdery mildew, and downy mildew and for the prevention or treatment of plant infestations by insect pests, including *Lepidoptera* larvae.

Powdery Mildew

Powdery mildews produce mycelium (fungal threads) that grow on the surface of plants without invading the underlying tissues. The fungi feed by sending haustoria, or root-like structures, into the epidermal (top) cells of the plant. The fungi overwinter on plant debris and in the spring produce spores that are moved to susceptible host tissue by splashing raindrops, wind or insect infestation Powdery mildews are characterized by patches of white talcum-powder-like growth. The disease is most commonly observed on the upper sides of the leaves, but can also affect the bottom sides of leaves, young stems, buds, flowers and fruit. Infected leaves may become distorted, turn yellow with small patches of green, and fall prematurely. Infected buds may fail to open.

Powdery mildews are host specific. They cannot survive without the proper host plant. Particular powdery mildew species are shown in Table 1 (below).

TABLE 1

Host Plants and Powdery Mildew Species.

| Hosts | Fungus species |
|---|---|
| Cucumbers, Endive, Lettuce, Melons, Potato, Pumpkin, Squash | *Erysiphe cichoracearum* |
| Broccoli, Brussels Sprouts, Cauliflower, And Other Cole Crops; Radicchio, Radishes, Turnips | *Erysiphe cruciferarum* |
| Tomatoes | *Erysiphe lycopersici* |
| Peas | *Erysiphe pisi* |
| Carrots, parsley, parsnips | *Erysiphe heraclei* |
| Beets | *Erysiphe polygoni* |
| Artichoke, eggplant, peppers, tomatillo, tomatoes | *Leveillula taurica* |
| Beans, black-eyed peas, cucurbits, okra | *Sphaerotheca fuliginea* |
| Strawberry | *Sphaerotheca macularis* |

*Botrytis*

*Botrytis* is an opportunistic pathogen that causes a fungal disease that infects a wide array of economically important crops and ornamental plants. There are several species of the fungus *Botrytis* which can cause blights; the most common is *Botrytis cinerea*. *Botrytis* is particularly difficult to control on fresh market tomatoes under field conditions due to its ability to colonize both foliage and stems of the plant canopy, as well as developing fruit. In addition, *Botrytis* can manifest itself as a basal stem lesion at the soil level and girdle plants, thereby killing the plant outright and reducing fruit yields. These characteristics make control with sprayable fungicides very difficult. Among vegetables and fruit, *Botrytis cinerea* infects asparagus, bean, beet, carrot, celery, chicory, crucifers, cucurbits, eggplant, endive, grape, lettuce, onion, pepper, potato, raspberry, rhubarb, rutabaga, shallot, strawberry, tomato, turnip, and others. *Botrytis cinerea* can infect many ornamental plants including: anemone, begonia, calendula, chrysanthemum, dahlia, dogwood, fuchsia, geranium, hawthorn, heather, hydrangea, marigold, pansy, periwinkle, petunia, rose, snapdragon, sunflower, sweet peat, violet, zinnia. Two other damaging *Botrytis* blight fungi have strict host preferences: *Botrytis paeoniae* infects peony, and *Botrytis tulipae* infects tulip causing the disease known as tulip fire.

Insect Pests

Virtually all field crops, plants, and commercial farming areas are susceptible to attack by one or more insect pests. Such pests may be targeted with an insecticide containing hop acids. Administration of compositions comprising hop acids can not only reduce infestation of plants by insects, but can reduce the infection of plants with pathogens that are associated with insect activity. In particular embodiments, insecticidal compositions of the invention are particularly useful for killing, repelling, or reducing an infestation of field crops, plants, commercial farming areas, including for example, any of those defined herein, with an insect or insect larva (e.g., a *Lepidoptera larva*).

Vegetable and cole crops, such as artichokes, kohlrabi, arugula, leeks, asparagus, lentils, beans, lettuce (e.g. head, leaf, romaine), beets, bok choy, malanga, broccoli, melons (e.g., muskmelon, watermelon, crenshaw, honeydew, cantaloupe), brussels sprouts, cabbage, cardoni, carrots, napa, cauliflower, okra, onions, celery, parsley, chick peas, parsnips, chicory, peas, Chinese cabbage, peppers, collards, potatoes, cucumber, pumpkins, cucurbits, radishes, dry bulb onions, rutabaga, eggplant, salsify, escarole, shallots, endive, soybean, garlic, spinach, green onions, squash, greens, sugar beets, sweet potatoes, turnip, swiss chard, horseradish, tomatoes, kale, turnips, and a variety of spices are sensitive to infestation by one or more of the following insect pests: alfalfa looper, armyworm, beet armyworm, artichoke plume moth, cabbage budworm, cabbage looper, cabbage webworm, corn earworm, celery leafeater, cross-striped cabbageworm, european corn borer, diamondback moth, green cloverworm, imported cabbageworm, melonworm, omnivorous leafroller, pickleworm, rindworm complex, saltmarsh caterpillar, soybean looper, tobacco budworm, tomato fruitworm, tomato hornworm, tomato pinworm, velvetbean caterpillar, and yellowstriped armyworm.

Likewise, pasture and hay crops such as alfalfa, pasture grasses and silage are often attacked by such pests as armyworm, beef armyworm, alfalfa caterpillar, European skipper, a variety of loopers and webworms, as well as yellowstriped armyworms.

Fruit and vine crops such as apples, apricots, cherries, nectarines, peaches, pears, plums, prunes, quince almonds, chestnuts, filberts, pecans, pistachios, walnuts, citrus, blackberries, blueberries, boysenberries, cranberries, currants, loganberries, raspberries, strawberries, grapes, avocados, bananas, kiwi, persimmons, pomegranate, pineapple, tropical fruits are often susceptible to attack and defoliation by achema sphinx moth, amorbia, armyworm, citrus cutworm, banana skipper, blackheaded fireworm, blueberry leafroller, cankerworm, cherry fruitworm, citrus cutworm, cranberry girdler, eastern tent caterpillar, fall webworm, filbert leafroller, filbert webworm, fruit tree leafroller, grape berry moth, grape leaffolder, grapeleaf skeletonizer, green fruitworm, gummosos-batrachedra commosae, gypsy moth, hickory shuckworm, hornworms, loopers, navel orangeworm, obliquebanded leafroller, omnivorous leafroller, omnivorous looper, orange tortrix, orangedog, oriental fruit moth, pandemis leafroller, peach twig borer, pecan nut casebearer, redbanded leafroller, redhumped caterpillar, rougliskinned cutworm, saltmarsh caterpillar, spanworm, tent caterpillar, thecla-thecla basilides, tobacco budworm, tortrix moth, tufted apple budmoth, variegated leafroller, walnut caterpillar, western tent caterpillar, and yellowstriped armyworm.

Field crops such as canola/rape seed, evening primrose, meadow foam, corn (field, sweet, popcorn), cotton, hops, jojoba, peanuts, rice, safflower, small grains (barley, oats, rye, wheat, etc.), sorghum, soybeans, sunflowers, and tobacco are often targets for infestation by insects including armyworm, asian and other corn borers, banded sunflower moth, beet armyworm, bollworm, cabbage looper, corn rootworm (including southern and western varieties), cotton leaf perforator, diamondback moth, European corn borer, green cloverworm, headmoth, headworm, imported cabbageworm, loopers (including *Anacamptodes* spp.), oblique banded leafroller, omnivorous leaftier, podworm, podworm, saltmarsh caterpillar, southwestern corn borer, soybean looper, spotted cutworm, sunflower moth, tobacco budworm, tobacco hornworm, velvetbean caterpillar, Bedding plants, flowers, ornamentals, vegetables and container stock are frequently fed upon by a host of insect pests such as armyworm, azalea moth, beet armyworm, diamondback moth, ello moth (hornworm), Florida fern caterpillar, Io moth, loopers, oleander moth, omnivorous leafroller, omnivorous looper, and tobacco budworm.

Forests, fruit, ornamental, and nut-bearing trees, as well as shrubs and other nursery stock are often susceptible to attack from diverse insects such as bagworm, blackheaded budworm, browntail moth, California oakworm, douglas fir tussock moth, elm spanworm, fall webworm, fruittree leafroller, greenstriped mapleworm, gypsy moth, jack pine budworm, mimosa webworm, pine butterfly, redhumped caterpillar, saddleback caterpillar, saddle prominent caterpillar, spring and fall cankerworm, spruce budworm, tent caterpillar, tortrix, and western tussock moth. Likewise, turf grasses are often attacked by pests such as armyworm, sod webworm, and tropical sod webworm.

Fungal Pests

Many economically important crops and ornamental plants are susceptible to fungal infestation, which causes a number of plant diseases. Hop compositions are useful for the prevention or treatment of fungal infestation of field crops, ornamental plants, or commercial farming areas. Examples of fungi or fungal disease causing pathogens include, without limitation, *Alternaria* (for example, *A. brassicola* and *A. solani*), which causes leaf blights in carrots and sugar beats, *Ascochyta* (for example, *A. pisi*), which causes *Ascochyta* blight in peas, chick peas, and turf, *Botrytis* (for example, *B. cinerea*), *Cercospora* (for example, *C. kikuchii* and *C. zaeamaydis*), which cause leaf blights in legumes and carrots, *Colletotrichum* sp. (for example, *C. lindemuthianum*), which causes anthracnose affecting peppers, beans, tomatoes, *Diplodia* (for example, *D. maydis*), which causes *Diplodia* ear rot and conifer blights, *Erysiphe* (for example, *E. graminis* f.sp. *graminis, E. necator,* and *E. graminis* f.sp. *hordei*), which causes powdery mildew, *Fusarium* (for example, *F. nivale, F. oxysporum, F. graminearum, F. solani, F. moniliforme,* and *F. roseum*), which can cause *Fusarium* root rots, wilts, and blights, *Gaeumanomyces* (for example, *G. graminis* f.sp. *tritici*), which causes take-all disease of cereals, *Helminthosporium* (for example, *H. turcicum, H. carbonum,* and *H. maydis*), *Macrophomina* (for example, *M. phaseolina* and *Maganaporthe grisea*), which causes charcoal rot, *Nectria* (for example, *N. heamatocacca*), which causes cankers affecting a variety of trees, *Peronospora* (for example, *P. manshurica, P. tabacina*), which causes downy mildew,

*Phoma* (for example, *P. betae*), which causes *Phoma* leaf spot/stem canker, *Phymatotrichum* (for example, *P. omnivorum*), which causes *Phymatotrichum* root rot, also known as cotton root rot, *Phytophthora* (for example, *P. cinnamomi, P. cactorum, P. phaseoli, P. parasitica, P. citrophthora, P. megasperma* f.sp. *sojae*, and *P. infestans*), which causes *Phytophthora* root rot or *Phytophthora* blight of peppers, cucurbits, eggplants and tomatoes, *Plasmopara* (for example, *P. viticola*), which causes downy mildew, *Podosphaera* (for example, *P. leucotricha*), which causes powdery mildew, *Puccinia* (for example, *P. sorghi, P. striiformis, P. graminis* f.sp. *tritici, P. asparagi, P. recondita*, and *P. arachidis*), which causes rust on cereals, turfgrass, and ornamental grasses, *Puthium* (for example, *P. aphanidermatum*), which causes *Puthium* root rot, *Pyrenophora* (for example, *P. tritici-repentens*), which is a necrotic fungus of barley, *Pyricularia* (for example, *P. oryzea*), which causes rice blast disease, *Pythium* (for example, *P. ultimum*), which causes *Pythium* root rot, damping off, and blight, *Rhizoctonia* (for example, *R. solani* and *R. cerealis*), which causes black scurf in potatoes and dry rot of sugar beets, *Scerotium* (for example, *S. rolfsii*), which causes Southern Blight, *Sclerotinia* (for example, *S. sclerotiorum*), which causes white mold diseases, *Septoria* (for example, *S. lycopersici, S. glycines, S. nodorum* and *S. tritici*), which causes leaf and fruit spot, *Thielaviopsis* (for example, *T. basicola*), which causes black root rot, *Uncinula* (for example, *U. necator*), which causes powdery mildew of grapes, *Venturia* (for example, *V. inaequalis*), which causes apple scab, *Verticillium* (for example, *V. dahliae* and *V. albo-atrum*), which causes tomato, potato, pepper, and egg-plant wilt. Hop compositions are useful for the prevention or treatment of plant fungal diseases or infestations.

Insecticide or Fungicide Formulations

The insecticide or fungicide compositions described may be made by formulating the isolated hop acids with the desired agriculturally-acceptable carrier. In one preferred embodiment, the hop acid compositions disclosed herein are useful as insecticides or fungicides for topical application to field crops, grasses, fruits and vegetables, lawns, trees, and/or ornamental plants. Alternatively, hop acids disclosed herein may be formulated as a spray, dust, powder, or other aqueous, atomized or aerosol for killing, repelling, or controlling plant pests, including fungi (e.g., *Botrytis, Erysiphe, Leveillula, Sphaerotheca, Rasutoria, Microsphaera, Podosphaera, Peronospora, Pseudoperonospora*, and *Plasmopara*) and insect larvae, particularly larvae of *Lepidoptera*.

The hop acid compositions disclosed herein may be used prophylactically to treat plants, plant growth materials, or greenhouses, or alternatively, may be administered to an environment once target insect larva or fungi have been identified in the particular environment to be treated. Regardless of the method of application, the amount of the active hops component(s) is applied at an effective amount, which will vary depending on such factors as, for example, the specific target insect larva or fungus to be controlled, the specific environment, location, plant, crop, or agricultural site to be treated, the environmental conditions, and the method, rate, concentration, stability, and quantity of application of the insecticidally or fungicidally-active composition. The formulations may also vary with respect to climatic conditions, environmental considerations, and/or frequency of application and/or severity of insect or fungal infestation. The compositions may be formulated prior to administration in an appropriate means such as lyophilized, freeze-dried, desiccated, or in an aqueous carrier, medium or suitable diluent, such as saline or other buffer. The formulated compositions may be in the form of a dust or granular material, a suspension in oil (vegetable or mineral), water, or oil/water emulsion, or as a wettable powder, or in combination with any other carrier material suitable for agricultural application. Suitable agricultural carriers can be solid or liquid and are well known in the art. An agriculturally-acceptable carrier includes but is not limited to, for example, adjuvants, inert components, dispersants, surfactants, tackifiers, and binders, that are ordinarily used in insecticide or fungicide formulation technology. Such carriers are well known to those skilled in insecticide or fungicide formulation. The formulations may be mixed with one or more solid or liquid adjuvants and prepared by various means, e.g., by homogeneously mixing, blending and/or grinding the insecticidal or fungicidal composition with suitable adjuvants using conventional formulation techniques.

The insecticidal or fungicidal compositions comprising hop acids or their derivatives may be produced by mixing compositions of the invention with various inert materials, such as inorganic minerals (phyllosilicates, carbonates, sulfates, phosphates, and the like) or botanical materials (powdered corncobs, rice hulls, walnut shells, and the like). The formulations may include spreader-sticker adjuvants, stabilizing agents, other pesticidal additives, or surfactants. Liquid formulations may be aqueous-based or non-aqueous and employed as foams, suspensions, emulsifiable concentrates, or the like. The ingredients may include biological agents, surfactants, emulsifiers, dispersants, or polymers.

Alternatively, the novel insecticidal or fungicidal compositions comprising hops acids are prepared by chemical synthesis or by purification from hops and then formulated for subsequent field application. Such agents may be either in crude lysates, suspensions, colloids, etc., or alternatively may be purified, refined, buffered, and/or further processed, before formulating in an active biocidal (e.g., insecticidal or fungicidal) formulation. Preferred formulations include any one or more of the following insecticidal or fungicidal compositions.

Oil Suspension or Oil-flowable Suspension

In one approach, the hop derivative is provided in an oil-based delivery system. The oil-hop derivative mix is deposited on a plant where it subsequently contacts and kills a fungus or insects, such as a *Lepidoptera* larvae. Alternatively, the composition repels an adult insect (e.g., *Lepidoptera*) or larvae. Oil release substrates include vegetable and/or mineral oils. In one embodiment, the substrate also contains a surface active agent that renders the composition readily dispersable in water; such agents include wetting agents, emulsifying agents, dispersing agents, and the like. In one embodiment, the insecticide or fungicide composition comprises an oil flowable suspension comprising a hop acid.

Water-Dispersible Granules

In another important embodiment, the insecticide or fungicide composition comprises a water dispersible granule. This granule comprises hop acids or their derivatives.

Powders, Dusts, Colloids, and Soap Formulations

For some applications, the insecticide or fungicide composition comprises a wettable powder, dust, crystal formulation, or colloidal concentrate. A powder or dust of the invention comprises hop acids or their derivatives. Such dry forms of the insecticidal or fungicidal compositions may be formulated to dissolve immediately upon wetting, or alternatively, dissolve in a controlled-release, sustained-release, or other time-dependent manner. Colloid comprising hop acids or their derivatives range from one nanometer to one micrometer. Colloidal compositions include colloidal aerosols, colloidal emulsions, colloidal foams, or colloidal suspensions or dispersions. Insecticidal or fungicidal soaps comprising hop acids or their derivatives are also provided. Any of the aforementioned compositions may be applied to, or ingested by, the target insect, and as such, may be used to control the numbers of insects, or the spread of such insects in a given environment. Alternatively, the composition is applied to or contacted with a target fungus or spore thereof.

Aqueous Suspensions

For some applications, the insecticide or fungicide composition comprises an aqueous suspension of hop acids or their derivatives. Such aqueous suspensions may be provided as a concentrated stock solution which is diluted prior to application, or alternatively, as a diluted solution ready-to-apply.

Emulsions

The insecticides or fungicides of the invention can also be provided as emulsions. Emulsion formulations can be found as water in oil (w/o) or oil in water (o/w). Droplet size can vary from the nanometer scale (colloidal dispersion) to several hundred microns. A variety of surfactants and thickeners are usually incorporated in the formulation to modify the size of the droplets, stabilize the emulsion, and modify the release of the active ingredient.

Multifunctional Formulations

In some embodiments, when the control of multiple pests is desired (e.g., multiple *Lepidoptera* species or fungal species), the insecticidal or fungicidal formulations described herein may comprise one or more chemical pesticides, (such as chemical pesticides, nematicides, fungicides, virucides, microbicides, amoebicides, insecticides, etc.), and/or one or more hop acids or their derivatives. The insecticidal or fungicidal agents may also be used in conjunction with other treatments, such as fertilizers, weed killers, cryoprotectants, surfactants, detergents, insecticidal soaps, dormant oils, polymers, and/or time-release or biodegradable carrier formulations that permit long-term dosing of a target area following a single application of the formulation. In addition, the formulations may be prepared in edible baits or fashioned into insect traps to permit feeding or ingestion by a target insect (e.g., insect larvae, such as *Lepidoptera* larvae) of the insecticide formulation. Other devices for insecticide or fungicide application include strips and other carriers, such as mulch.

The insecticidal or fungicidal compositions of the invention may also be used in consecutive or simultaneous application to an environmental site singly or in combination with one or more additional insecticides, pesticides, chemicals, fertilizers, or other compounds.

Application Methods and Effective Rates

The insecticidal or fungicidal compositions of the invention are applied to the environment of the target insect (e.g., *Lepidoptera*) or fungus, typically onto the foliage of the plant or crop to be protected, by conventional methods, preferably by spraying. The strength and duration of application will be set with regard to conditions specific to the particular pest(s), crop(s) to be treated and particular environmental conditions. The proportional ratio of active ingredient to carrier will naturally depend on the chemical nature, solubility, and stability of the insecticidal composition.

Other application techniques, including dusting, sprinkling, soil soaking, soil injection, seed coating, seedling coating, foliar spraying, aerating, misting, atomizing, fumigating, aerosolizing, and the like, are also feasible and may be required under certain circumstances such as e.g., insects that cause root or stalk infestation, or for application to delicate vegetation or ornamental plants. These application procedures are also well-known to those of skill in the art.

The concentration of an insecticidal or fungicidal composition that is used for environmental, systemic, topical, or foliar application will vary widely depending upon the nature of the particular formulation, means of application, environmental conditions, and degree of insecticidal or fungicidal activity. Typically, the insecticidal or fungicidal composition comprising hop acids (e.g., alpha acids, beta acids, or combinations thereof) will be present in the applied formulation at a concentration of at least about 1%, 5%, 10%, 20%, 30%, 40%/G, 50%, 60%, 70%, 80%, 90%, or 99% by weight or volume. Dry formulations of hop acids or their derivatives may be from about 1% to about 99% or more by weight of the composition (e.g., 1%, 5%, 10%, 20%, 30%, 40%, 50%, 60%, 70%, 80%, 90%, 99%) or more of the active ingredient by weight.

An insecticidal or fungicidal formulation described herein may be administered to a particular plant or target area in one or more applications as needed, with a typical field application rate per hectare ranging on the order of about 50, 100, 200, 300, 400, or 500 g/hectare of active ingredient, or alternatively, 600, 700, 800, 900, or 1000 g/hectare may be utilized. In certain instances, it may even be desirable to apply the insecticidal or fungicidal formulation to a target area at an application rate of about 1000, 2000, 3000, 4000, 5000 g/hectare or even as much as 7500, 10,000, or 15,000 g/hectare of active ingredient.

Screens for Insecticides and Fungicides Comprising Hop Acids

As discussed above, hop acids or their derivatives are useful, for example, for inhibiting growth, reproduction, or molting in a insect (e.g., *Lepidoptera*) or other insect or for repelling an adult or larval insect (e.g., *Lepidoptera*). Such hop acids or their derivatives may be, for example, applied ectopically to a plant at a level that is sufficient to inhibit insect infestation in the plant. Evaluation of the level of insect protection conferred to a plant by application or administration of hop acids or their derivatives is determined according to conventional methods and assays.

In one embodiment, a plant is contacted with a hop acids or their derivatives present in an excipient, such that hop acids or their derivatives is present in or on the plant (e.g., in or on the roots, leaves, stems, fruit, flowers, or vegetative tissues). A parasitic insect, such as a *Lepidoptera* larvae, is introduced to the plant under controlled conditions (for example, standard levels of temperature, humidity, and/or soil conditions). After a period of incubation sufficient to allow the growth and reproduction of a harmful insect on a control plant not contacted with hop acids or their derivatives, insects or their progeny are evaluated for their level of growth, viability, or reproduction according to conventional experimental methods. For example, the number of insects or their progeny is recorded every twenty-four hours for seven days, fourteen days, twenty-one days, or twenty-eight days or longer after inoculation. From these data, levels of inhibition of harmful insects are determined. Hop acids that inhibit the hatching, growth, viability, or reproduction of a harmful insect are taken as being useful in the invention. In another embodiment, the level of plant damage is determined according to standard methods on the plant contacted with hop acids or their derivatives relative to a control plant not contacted with the hop acids or their derivatives. Hop acids or their derivatives that inhibit plant damage or increase the amount of marketable fruit or vegetables are taken to be useful in the methods of the invention. Screening methods are used to identify concentrations of hop acids or their derivatives that will effectively inhibit the growth, proliferation, survival or transmission of a fungus.

Screens for Fungicidal Activity

Products comprising hop acids or their derivatives are used to control fungal infestation reduce, stabilize, or slow the growth of a fungus population on a plant or in a field or inhibit the growth, survival, proliferation, or other biological function of fungus. Methods for measuring infestation are known in the art. A number of parameters can be indicative of the level of fungal infestation present in a plant or plant population: the amount of fungal damage present in a plant sample; the amount of marketable fruit obtained from a treated field relative to a control field innoculated with a fungal infestation; thus, fruit size, weight, or the presence of blemishes can be used as another measure of infestation; the amount of fruit produced in an infected field may be less than that produced in a healthy field; accordingly, fruit production could serve as one measure of the level of infestation; and finally, severe infestations may result in loss of substantial amounts of marketable fruit In one embodiment, a fungicide of the invention reduces the level of infestation in a plant, plant population, or field by at least 10%, 25%, 50%, 75% or even by 100%. In another embodiment, a fungicide of the invention inhibits or prevents at least 50%, 60%, or even 75% or 100% of fuingal growth. Screening methods are used to identify concentrations of hop acids or their derivatives that will effectively inhibit the growth, proliferation, survival or transmission of a fingus.

Screens for Insecticidal Activity

Commuercial products that are currently being used to control insect or fingal infestation can have adverse effects on humans and the environment. In contrast to conventional insecticides or fungicides, compositions of the invention contain safe natural products derived from hops. In one aspect, the compound or derivative is an isolated compound (e.g., alpha acids, beta acids, or combinations thereof). Hops have been used for centuries to flavor beer, thus, formulations comprising hop derivatives are generally safe. In contrast to conventional insecticides and fungicides, insecticidal or fungicidal compositions of the invention do not adversely affect humans or the environment, and the residues thereof present no toxicity concerns when present on produce intended for human consumption.

Insecticidal compositions of the invention contain concentrations of hop derivatives that are effective in killing or disrupting the biological functioning of an insect. In one approach, insect (e.g., *Lepidoptera*) larvae are exposed to varying concentrations of hop derivatives to identify those concentrations that reduce plant infestation using any of the aforementioned criteria. Screening assays are used to determine the concentration of a composition of the invention that reduces the number of larvae that grow to reproductive maturity, preferably, the reduction is by at least 25%, 50%, 75%, 85%, 95% or 100%. Alternatively, compositions of the invention reduce infestation by repelling an adult insect (e.g., *Lepidoptera*) or larval insect. In one embodiment, compositions of the invention reduce the number of adult *Lepidoptera* that deposit eggs on plants treated with compositions of the invention, that reduce the number of eggs that hatch on treated plants, that interfere with the growth of larvae on treated plants, that repel larvae or adult *Lepidoptera*, or that otherwise reduce *Lepidoptera* associated damage to treated plants.

Hop Derivatives

A hop derivative is a compound that occurs naturally in a hop plant (*Humulus lupulus*) or is chemically derived (either through natural biosynthetic processes (e.g., living organism metabolism (e.g., mammal, plant, bacteria)) or by synthetic processes using human intervention (e.g., chemical synthesis). Compositions of the invention include one or more compounds derived from hops. Of particular interest are the hop acids. Hops contain two major organic acid classes, alpha acids and beta acids. Hop acids are the bitter acid components of hops that are used in beer making. There are three major analogs for alpha acids, humulone, cohumulone, and adhumulone, and three major analogs for beta acids, lupulone, colupulone, and adhupulone. The percentages of the analogs present in the alpha acids and beta acids are variety-dependent. Thus, hop derivatives and hop products typically contain one or a mixture of these analogs. The percentage of analog present is dependent on the hop variety used to produce the derivative or product. Alpha acids and beta acids can be prepared by purification from natural hops and also by chemical synthesis according to traditional methods. Exemplary hop derivatives include alpha acids, beta acids, hexahydrobeta acids, rhoisoalpha acids, isoalpha acids, tetrahydroisoalpha acids, hexahydroisoalpha acids, magnesium salts of rhoisoalpha acids and magnesium salts of beta acids. Compositions comprising hop derivatives are also available commercially. John I. Haas, Inc. products containing hop derivatives include Betacide, Redihop®, Isohop®, Tetrahop Gold®, Hexahop Gold®, MgRIAA and MgBeta. The active ingredients in these products are alpha acids, beta acids, rhoisoalpha acids (RIAA), isoalpha acids (IAA), tetrahydroisoalpha acids (THIAA), hexahydroisoalpha acids (HHIAA), magnesium salts of rhoisoalpha acids (MgRIAA) and magnesium salts of beta acids MgBA), respectively. These products and/or hop derivatives are typically diluted to a desired concentration for use in the methods of the invention.

Plant extracts are often used for the purification of compounds from plants (e.g., hops). An extract can be prepared by drying and subsequently cutting or grinding the dried material. The term "extract" refers to a concentrated preparation of the essential constituents of a plant, such as hops. Typically, an extract is prepared by drying and powderizing the plant. Optionally, the plant, the dried plant or the powderized plant may be boiled in solution. The extract may be used in liquid form, or it may be mixed with other liquid or solid herbal extracts. Alternatively, the extract may be obtained by further precipitating solid extracts from the liquid form. The extraction process may then be performed with the help of an appropriate choice of solvent, typically ethanol/water mixture, methanol, butanol, iso-butanol, acetone, hexane, petroleum ether or other organic solvents by means of maceration, percolation, repercolation, counter-current extraction, turbo-extraction, or by carbon-dioxide supercritical (temperature/pressure) extraction. The extract may then be further evaporated and thus concentrated to yield by means of air drying, spray drying, vacuum oven drying, fluid-bed drying or freeze-drying, the extract product.

Crude extracts are tested for insecticidal or fungicidal activity as described herein Further fractionation of a positive lead extract having insecticidal or fungicidal activity is necessary to isolate chemical constituents responsible for the observed effect. Thus, the goal of the extraction, fractionation, and purification process is the careful characterization and identification of a chemical entity within the crude extract that disrupts an insect (e.g., *Lepidoptera*) or fungal biological function. Methods of fractionation and purification of such heterogeneous extracts are known in the art. If desired, compounds shown to be useful as insecticides or fungicides are chemically modified according to methods known in the art.

Numerous methods are available for the chemical synthesis of candidate compounds. Such compounds can be synthesized from readily available starting materials using standard synthetic techniques and methodologies known to those of ordinary skill in the art. Synthetic chemistry transformations and protecting group methodologies (protection and deprotection) useful in synthesizing the compounds identified by the methods described herein are known in the art and include, for example, those such as described in R. Larock, Comprehensive Organic Transformations, VCH Publishers (1989); T. W. Greene and P. G. M. Wuts, Protective Groups in Organic Synthesis, 2nd ed., John Wiley and Sons (1991); L. Fieser and M. Fieser, Fieser and Fieser's Reagents for Organic Synthesis, John Wiley and Sons (1994); L. Paquette, ed., Encyclopedia of Reagents for Organic Synthesis, John Wiley and Sons (1995); and M. Verzele and D. De Keukeleire, Chemistry and Analysis of Hop and Beer Bitter Acids, Elsevier: Amsterdam (1991). Chemically synthesized alpha and beta acids can be separated from a reaction mixture and further purified by a method such as column chromatography, high pressure liquid chromatography, or recrystallization. As can be appreciated by the skilled artisan, further methods of synthesizing the compounds herein will be evident to those of ordinary skill in the art. Additionally, the various synthetic steps may be performed in an alternate sequence or order to give the desired compounds.

The compounds of this invention may contain one or more asymmetric centers and thus occur as racemates and racemic mixtures, single enantiomers, individual diastereomers and diastereomeric mixtures. All such isomeric forms of these compounds are expressly included in the present invention. The compounds of this invention may also be represented in multiple tautomeric forms, in such instances, the invention expressly includes all tautomeric forms of the compounds described herein (e.g., alkylation of a ring system may result in alkylation at multiple sites, the invention expressly includes all such reaction products). All such isomeric forms of such compounds are expressly included in the present invention. All crystal forms of the compounds described herein are expressly included in the present invention. As used herein, the compounds of this invention, including the compounds of formulae described herein, are defined to include derivatives. Derivatives include compounds of the invention that are modified by appending appropriate functionalities to enhance desired properties.

Acceptable salts of the compounds of this invention include those derived from acceptable inorganic and organic acids and bases. Examples of suitable acid salts include acetate, adipate, alginate, aspartate, benzoate, benzenesulfonate, bisulfate, butyrate, citrate, camphorate, camphorsulfonate, digluconate, dodecylsulfate, ethanesulfonate, formate, fumarate, glucoheptanoate, glycolate, hemisulfate, heptanoate, hexanoate, hydrochloride, hydrobromide, hydroiodide, 2-hydroxyethanesulfonate, lactate, maleate, malonate, methanesulfonate, 2-naphthalenesulfonate, nicotinate, nitrate, palmoate, pectinate, persulfate, 3-phenylpropionate, phosphate, picrate, pivalate, propionate, salicylate, succinate, sulfate, tartrate, thiocyanate, tosylate and undecanoate. Other acids, such as oxalic acid, may be employed in the preparation of salts useful as intermediates in obtaining the compounds of the invention and their acceptable acid addition salts. Salts derived from appropriate bases include alkali metal (e.g., sodium), alkaline earth metal (e.g., magnesium), ammonium and N-(alkyl)$_4^+$ salts. This invention also envisions the quaternization of any basic nitrogen-containing groups of the compounds disclosed herein. Water or oil-soluble or dispersible products may be obtained by such quaternization.

Lower or higher doses than those recited herein may be required to effectively kill insect (e.g., Lepidoptera) larva or fungi. Specific dosage and treatment regimens are determined empirically as described herein. Compositions of the invention are also useful for preventing the establishment of a insect (e.g., Lepidoptera) or fungal infestation, for treating an established insect (e.g., Lepidoptera) or fungal infestation, and for maintaining the health of a plant population or field previously treated for an infestation.

Aqueous Compositions of Hop Acids

Stable aqueous solutions of hop acids can be prepared by the selection of appropriate concentration and pH as described herein, and at U.S. Patent Publication Nos. 20050220914, 20030129270, and 20020051804, each of which is incorporated herein by reference.

Hop acid formulations are useful as treatment formulations for plant pests. The invention provides 1%, 5%, 10%, 30%, 50%, 60%, 75%, 85%, and 95% solutions of hop acids diluted with water to create stable aqueous emulsions. Stable aqueous solutions of hop acids can be prepared by adjusting the hop acids concentration and pH. Further, it is possible to convert these solutions into stable aqueous emulsions (i.e., colloidal suspensions in water) that will not separate over time, with the added advantage that the emulsions can be diluted with water, as required, by the end user for spraying onto plants for pest control. Although the emulsions are stable, they are also susceptible to film or residue creation when diluted with hard water. Such film formation can clog spray applicators. This problem can be eliminated by adding liquid soap to the treatment solution at a low concentration of approximately 0.1%, 0.25%, 0.5%, 1%, 2% or more.

Kits

The invention provides kits for the treatment or prevention of Lepidopteran or fungal infestation. In one embodiment, the kit includes a composition containing an effective amount of a hop derivative in a form suitable for delivery to a site of infestation (e.g., plant or field). In some embodiments, the kit comprises a container which contains a fungicide or insecticide; such containers can be boxes, ampules, bottles, vials, tubes, bags, pouches, blister-packs, or other suitable container forms known in the art. Such containers can be made of plastic, glass, laminated paper, metal foil, or other materials suitable for holding miticides.

If desired the fungicide or insecticide of the invention is provided together with instructions for administering it to a site of infestation. The instructions will generally include information about the use of the composition for the treatment or prevention of Lepidoptera or fungal infestation. In other embodiments, the instructions include at least one of the following: description of the insecticide or fungicide; dosage schedule and administration for treatment or prevention of an insect or fungal infestation; precautions; warnings; description of research studies; and/or references. The instructions may be printed directly on the container (when present), or as a label applied to the container, or as a separate sheet, pamphlet, card, or folder supplied in or with the container.

EXAMPLES

Compositions of the invention are useful for the prevention or treatment of insecticidal infestations in a plant, plant population, or field. As described at U.S. Patent Publication Nos. 20050220914, 20030129270, and 20020051804, hop acid compositions are useful for the inhibition of powdery mildew caused by *Podosphaera macularis* on hops *Humulus lupulus*, of *Phytophthora infestans* on potato, *Solanum tuberosum*, or the powdery mildew organism *Uncinula necator* on grapes, *Vitis vinifera*. As reported herein, compositions of the invention are generally useful for the control of fungal organisms or insect larvae affecting economically important agricultural crops and ornaments.

Example 1

Botrytis Control

Botrytis is an opportunistic fungal plant pathogen that is very difficult to control on fresh market tomatoes under field conditions due to its ability to colonize both foliage and stems of the plant canopy, as well as of the developing fruit. In addition, Botrytis can manifest itself as a basal stem lesion at the soil level and girdle plants, thereby killing the plant outright and reducing yields accordingly. These characteristic of Botrytis make control with sprayable fungicides very difficult and sometimes even more difficult to evaluate among several under experimental conditions. Nevertheless, this experiment established that application of hop acids and their derivatives can be used to treat or prevent Botrytis cinerea infestation of susceptible fresh market tomato planting.

Susceptible tomato plants were overhead misted to encourage disease establishment. These studies were conducted in San Luis Obispo, Calif. where normal coastal conditions also encourage spore survival. Experiment carried out on 0.01 acre. Plot dimension is 6.67 feet by 20 feet; row spacing is 3.33 feet; and plant spacing is 18". Plants received 4 treatments of BetaCide and of a positive control, the agricultural chemical fungicide Bravo Ultrex, which contains Chlorothalonil (tetrachloroisophthalonitrile 82.5%). BetaCide was applied at 10% v/v on a 7 day schedule. Bravo Ultrex was applied at 1.4 lb/a (pound per acre) on a 7 day schedule. Conditions in two untreated control plots were also monitored.

Treatment applications were performed using a $CO_2$ backpack sprayer. The spray boom incorporated six D4 nozzles with #25 spinners and was operated at a pressure of 40-50 psi. Treatments were applied at a dilution of 80-100 GPA (gallon per acre). The boom size was adjusted according to the growth stage of the tomatoes to ensure a thorough foliar coverage. The diagram in FIG. 1 illustrates the boom used.

Figure 2:
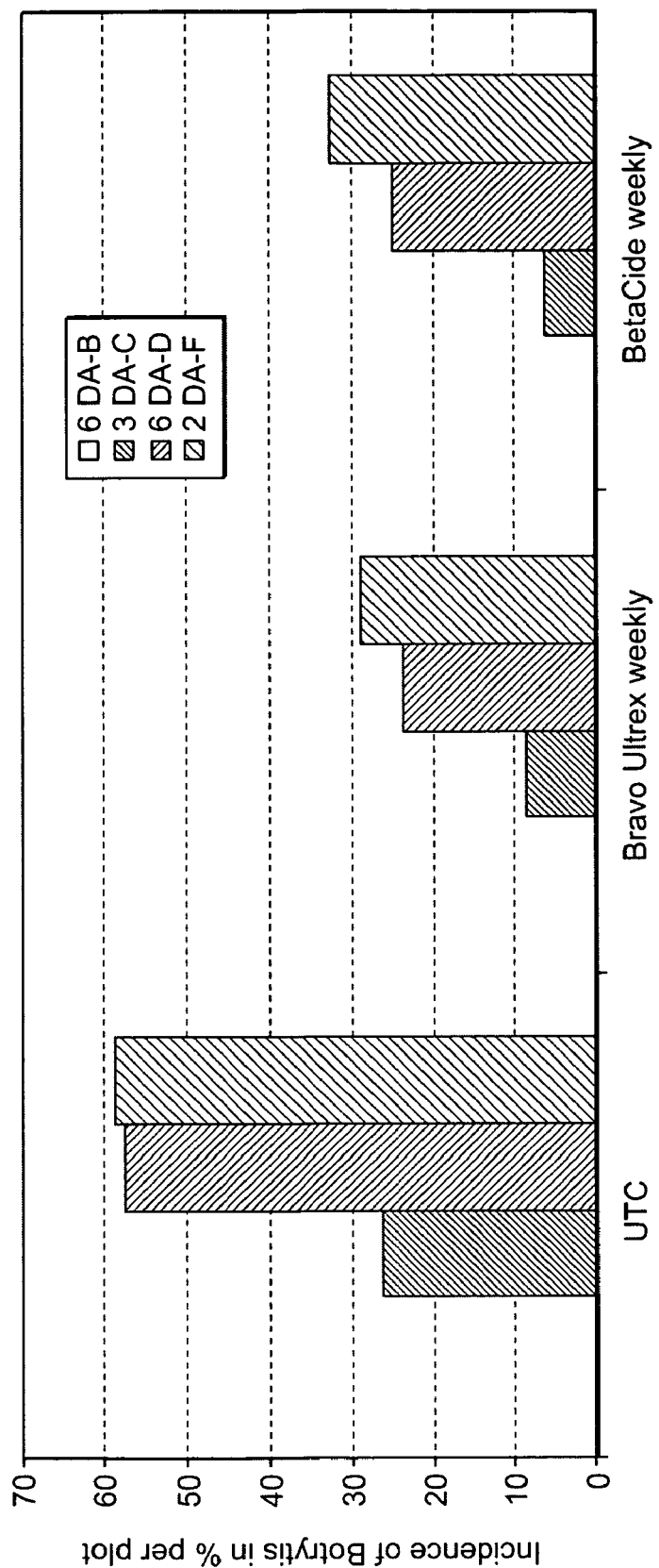
FIG. 2 is a graph that shows *Botrytis cinerea* disease incidence in percent per plot. Throughout these figures, "UTC" denotes untreated control.

The plots were evaluated by determining the disease incidence per plot and severity. Incidence of Botrytis infection was evaluated in percent per plot (FIG. 2).

Figure 3:
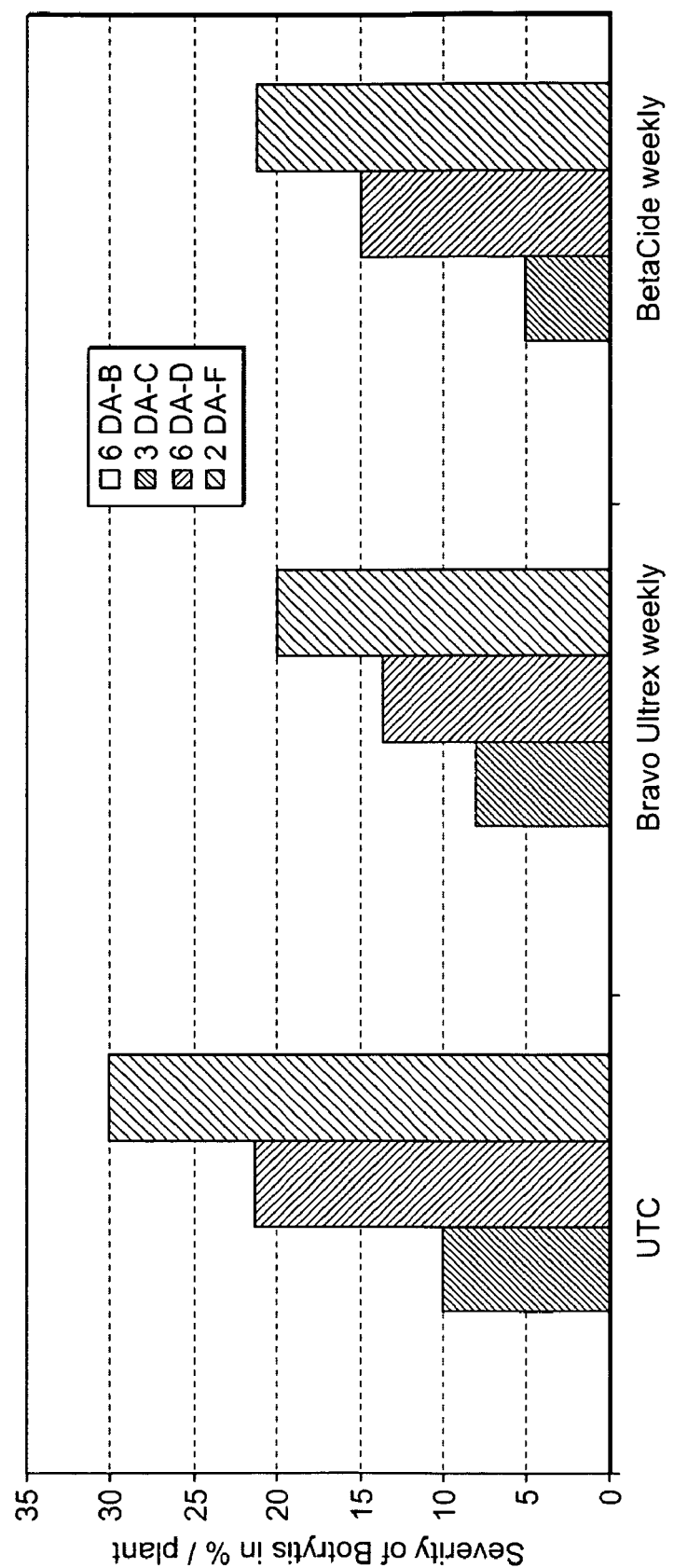
FIG. 3 is a graph that shows *Botrytis* disease severity that illustrates the percent of plant area infected with *Botrytis*.
Figure 4:
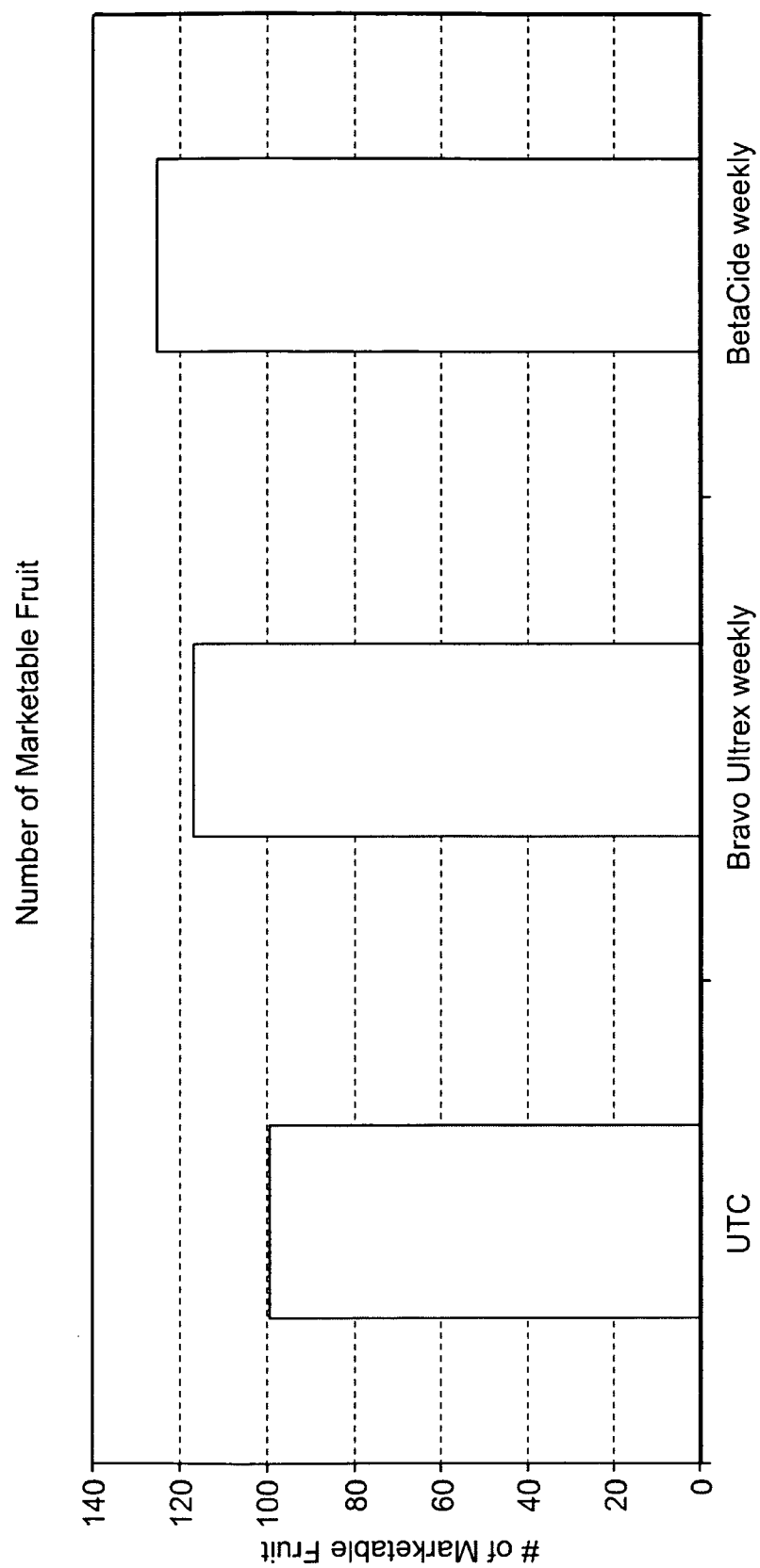
FIG. 4 is a graph that shows the number of marketable fruit per plot.
Figure 5:
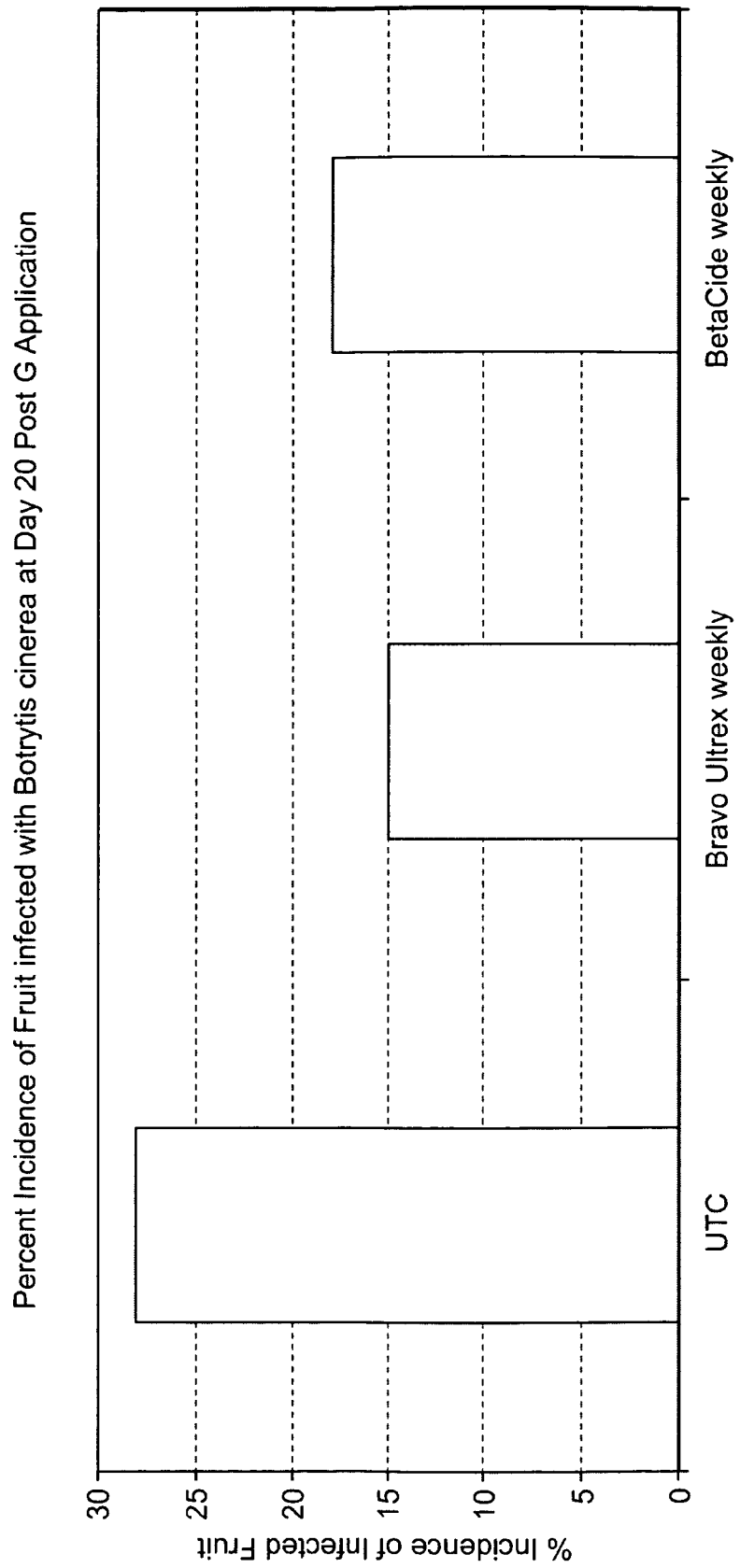
FIG. 5 is a graph that shows fruit infected with *Botrytis cinerea* (% per plot at day 20 post "G" application, where G is the application date).

The incidence reflects the percentage of infected plants per plot. The severity shows the percentage of plant area affected (FIG. 3). Disease incidence was also evaluated by counting the number of fruit with Botrytis cinerea out of twenty randomly selected fruit per plot (FIG. 4). The yield evaluation consisted of a count of marketable fruit and the determination of the percentage of fruit infected with Botrytis. Phytotoxicity was evaluated throughout the study. Tables 2-5 and FIGS. 2-5 show the results of these studies.

TABLE 2

Disease Incidence in Percent of Plot Affected

| Trt No | Treatment Name | Rate | Rate Unit | Appl. Code | Jul. 11, 2005 6 DA-B | Jul. 15, 2005 3 DA-C | Jul. 26, 2005 6 DA-D | Aug. 5, 2005 2 DA-F |
|---|---|---|---|---|---|---|---|---|
| 1 | UTC | | | A-G | 0 a | 26.25 a | 57.5 a | 58.75 a |
| 7 | Bravo Ultrex | 1.4 | lb/a | A-G | 0 a | 8.75 b | 23.75 a | 28.75 b |
| 8 | BetaCide | 10 | % v/v | A-G | 0 a | 6.25 b | 25 a | 32.5 b |
| 9 | UTC2 | | | A-G | 0 a | 15 ab | 51.25 a | 56.25 a |

Applications codes denote the application date;
and DA denotes days after application date. For example, 6-DA-B denotes 6 days after application B (which was on Jul. 5, 2005).
"a" denotes no difference.
"b" denotes a significant difference.
Data having two different letters show a statistical difference.
Means followed by same letter do not significantly differ (P = .05, Student-Newman-Keuls);
Mean comparisons performed only when AOV Treatment P(F) was significant at mean comparison OSL.
This convention is followed throughout the application.

TABLE 3

Disease Severity in Percent per Plant Affected

| Trt No. | Treatment Name | Rate | Rate Unit | Appl. Code | Jul. 11, 2005 6 DA-B | Jul. 15, 2005 3 DA-C | Jul. 26, 2005 6 DA-D | Aug. 5, 2005 2 DA-F |
|---|---|---|---|---|---|---|---|---|
| 1 | UTC | | | A-G | 0 a | 10 a | 21.25 a | 30 a |
| 7 | Bravo Ultrex | 1.4 | lb/a | A-G | 0 a | 8.13 a | 13.75 a | 20 a |
| 8 | BetaCide | 10 | % v/v | A-G | 0 a | 5 a | 15 a | 21.25 a |
| 9 | UTC2 | | | A-G | 0 a | 10 a | 23.75 a | 27.5 a |

TABLE 4

Number of Marketable Fruit.
Number of Marketable Fruit per Plot

| Trt No. | Treatment Name | Rate | Rate Unit | Appl. Code | Aug. 30, 2005 @ Harvest |
|---|---|---|---|---|---|
| 1 | UTC | | | A-G | 99.75 |
| 7 | Bravo Ultrex | 1.4 | lb/a | A-G | 117.5 |
| 8 | BetaCide | 10 | % v/v | A-G | 125.5 |
| 9 | UTC2 | | | A-G | 120.25 |

TABLE 5

The disease incidence of fruit infected with *Botrytis cinerea* calculated in % per plot.

| Trt No. | Treatment Name | Rate | Rate Unit | Appl. Code | Aug. 30, 2005 @ Harvest |
|---|---|---|---|---|---|
| 1 | UTC | | | A-G | 28 a |
| 7 | Bravo Ultrex | 1.4 | lb/a | A-G | 15 c |
| 8 | BetaCide | 10 | % v/v | A-G | 18 bc |
| 9 | UTC2 | | | A-G | 23 ab |

Under these conditions, 58.75% of plants were infected with *Botrytis cinerea* in untreated controls fields at the end of the 10-week study; In contrast, the BetaCide treatment reduced the incidence of *Botrytis* by 50% or more relative to the untreated control plot. Plots treated with hop acids had numerically lower *Botrytis* incidence than other fungicide programs studied. Plant samples were taken at approximately weekly intervals to assess the percentage of *Botrytis* infected plants in each plot. *Botrytis* infestation was reduced at all time points by Betacide. BetaCide treated plots also numerically outyielded all other treatments as measured in the number of marketable fruit produced. BetaCide has efficacy against this *Botrytis cinerea* and that if used for *Botrytis* control, it may have the added benefit of suppressing other diseases as well.

Example 2

*Lepidoptera* Control

Figure 6:
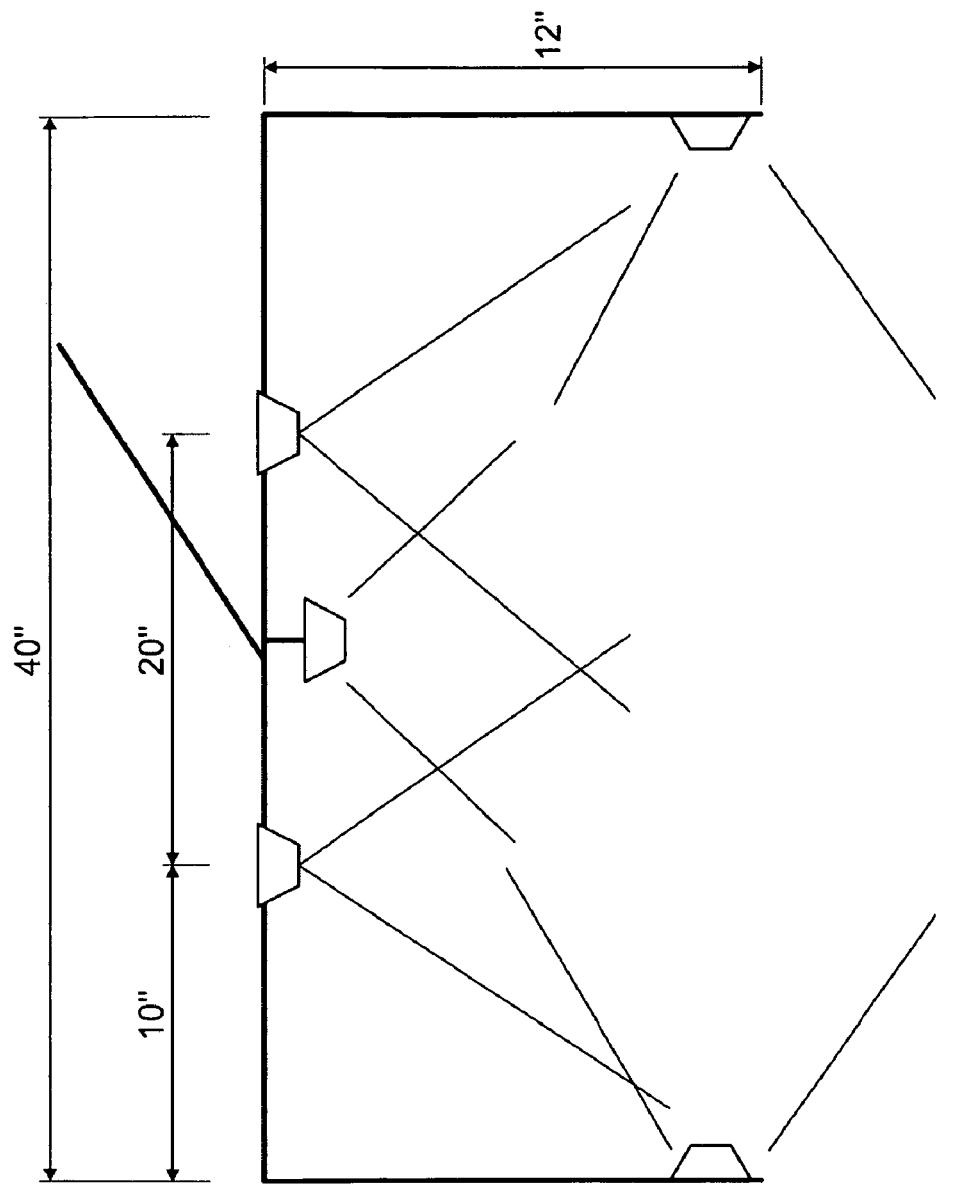
FIG. 6 is a schematic diagram of a boom. The nozzles are depicted as quadrangles.

This study was done in summer of 2005 at the research farm of Pacific Ag Research in San Luis Obispo, Calif. to determine the efficacy of BetaCide at a rate of 10% for control of *Lepidoptera* pests on fresh tomatoes. Avaunt and Success were used as positive controls. Results with BetaCide, Avaunt, and Success were compared with those in 2 untreated control plots. The pest pressure was moderate. Insecticides were applied in four applications every 7-15 days. BetaCide was applied at 10% volume per volume in water (v/v); Avaunt was applied at 167 g/ha; Success was applied at 208 ml/ha. Treatment applications were performed using a $CO_2$ backpack sprayer. The spray boom incorporated five D4 nozzles with #25 spinners and was operated at a pressure of 40-50 psi. Treatments were applied at a dilution of 65-85 GPA. The boom size was adjusted according to the growth stage of the plant to ensure a thorough foliar coverage. The diagram in FIG. 6 illustrates the boom used.

Figure 7:
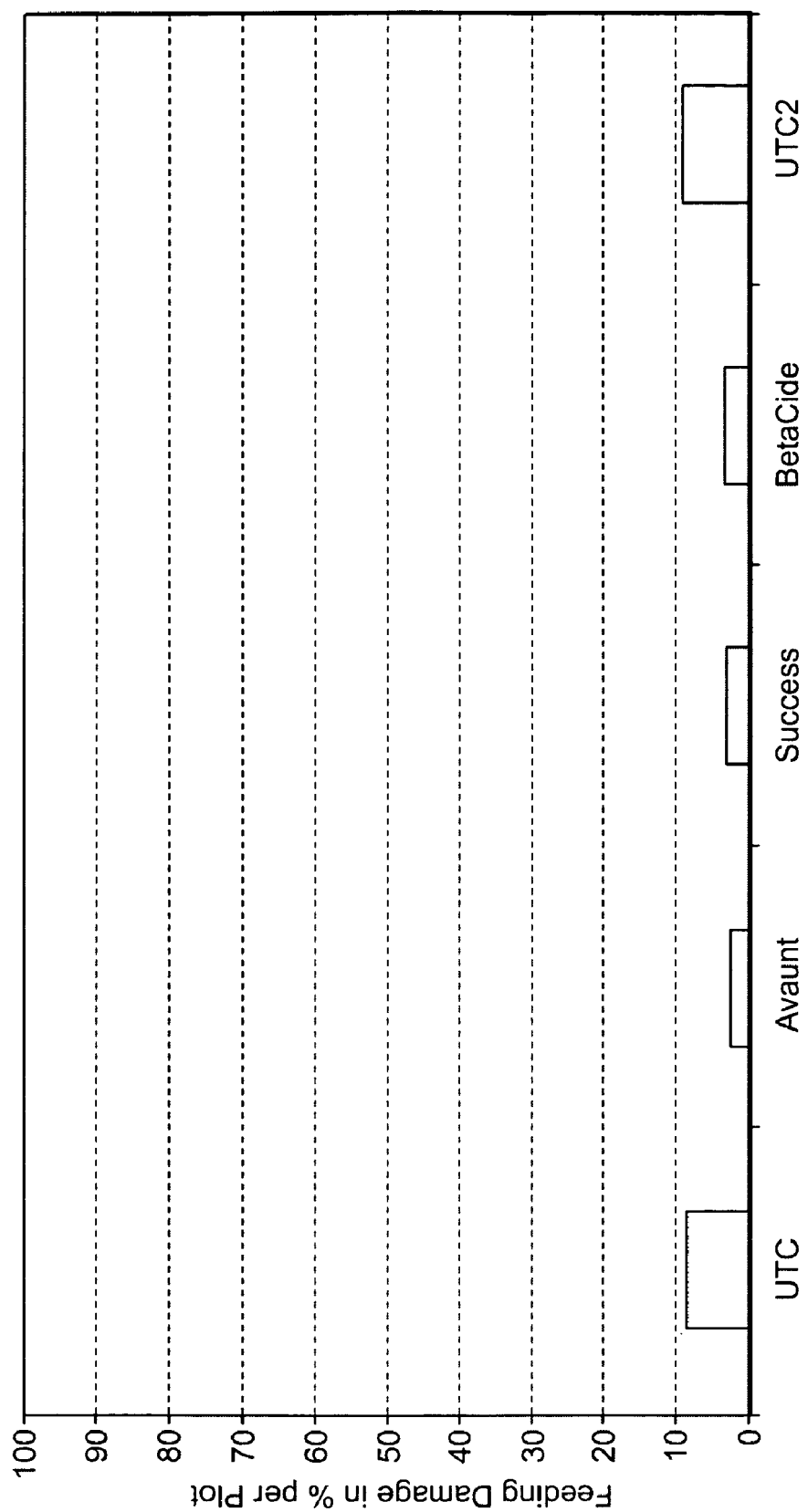
FIG. 7 illustrates the percent of insect feeding damage per plot.
Figure 8:
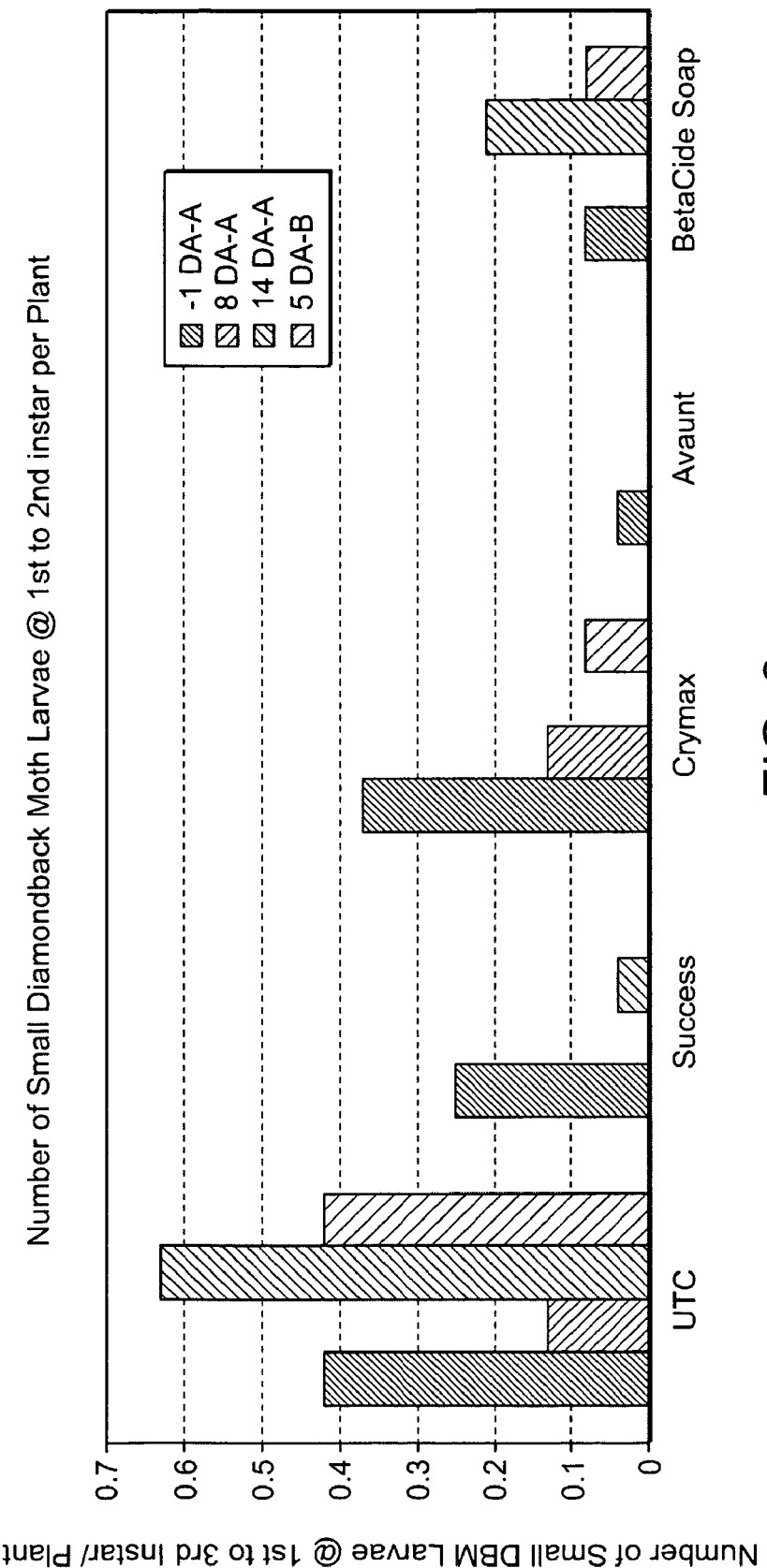
FIG. 8 illustrates the number of $1^{th}$ to $2^{nd}$ instar diamondback moth larvae per plant.
Figure 9:
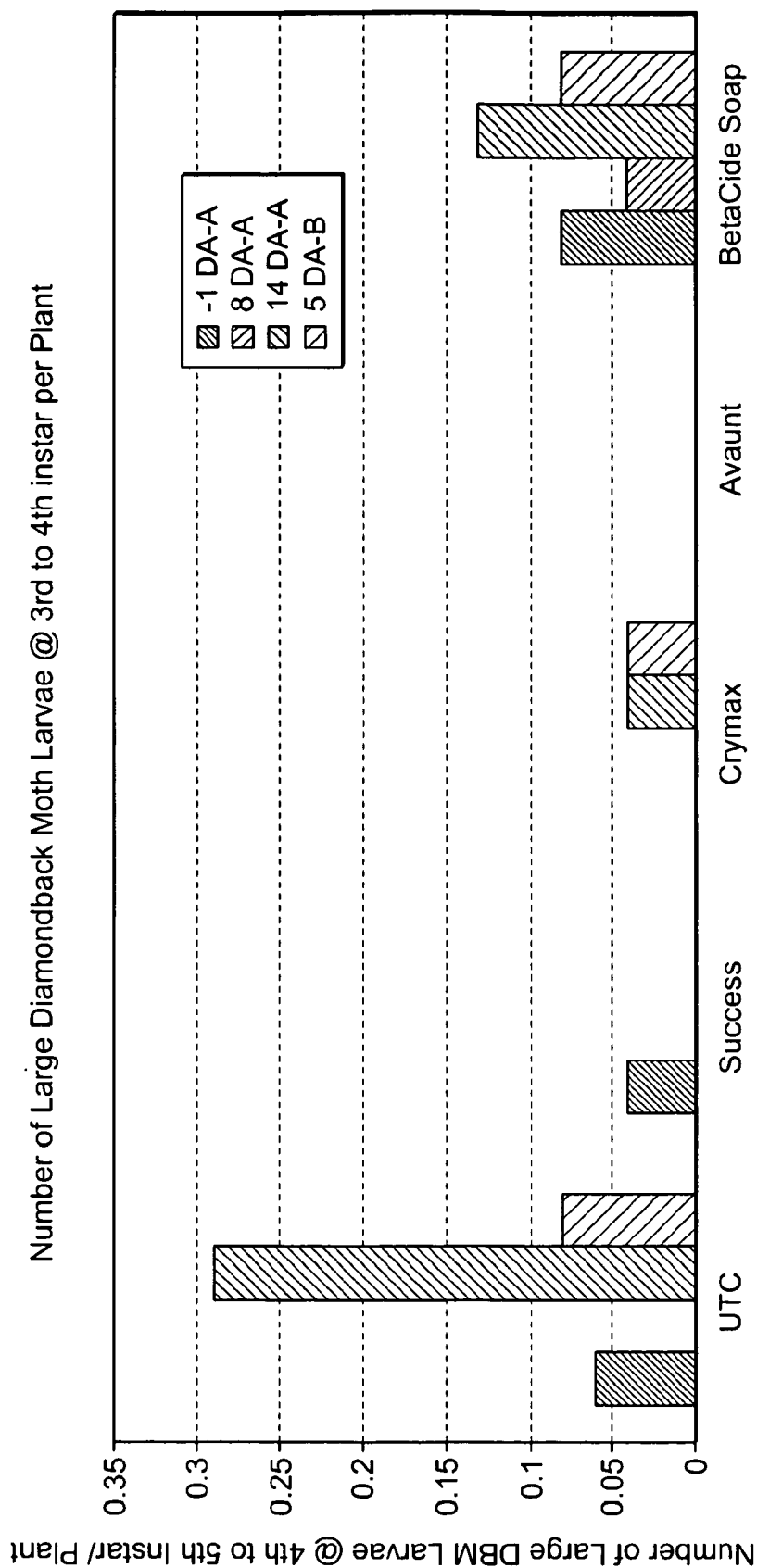
FIG. 9 illustrates the number of $3^{rd}$ to $4^{th}$ diamondback moth larvae per plant.
Figure 10:
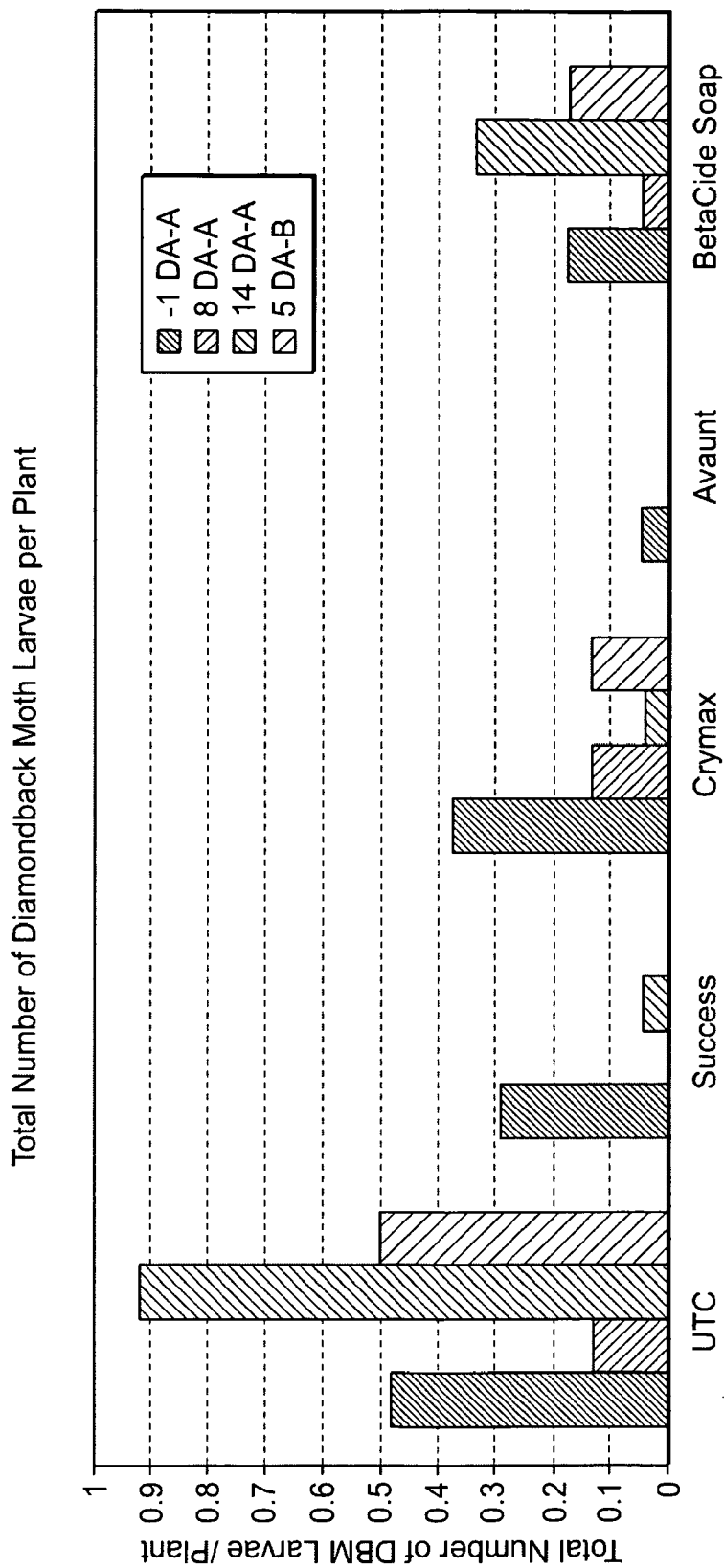
FIG. 10 illustrates the number of total number of diamondback moth larvae per plant.
Figure 11:
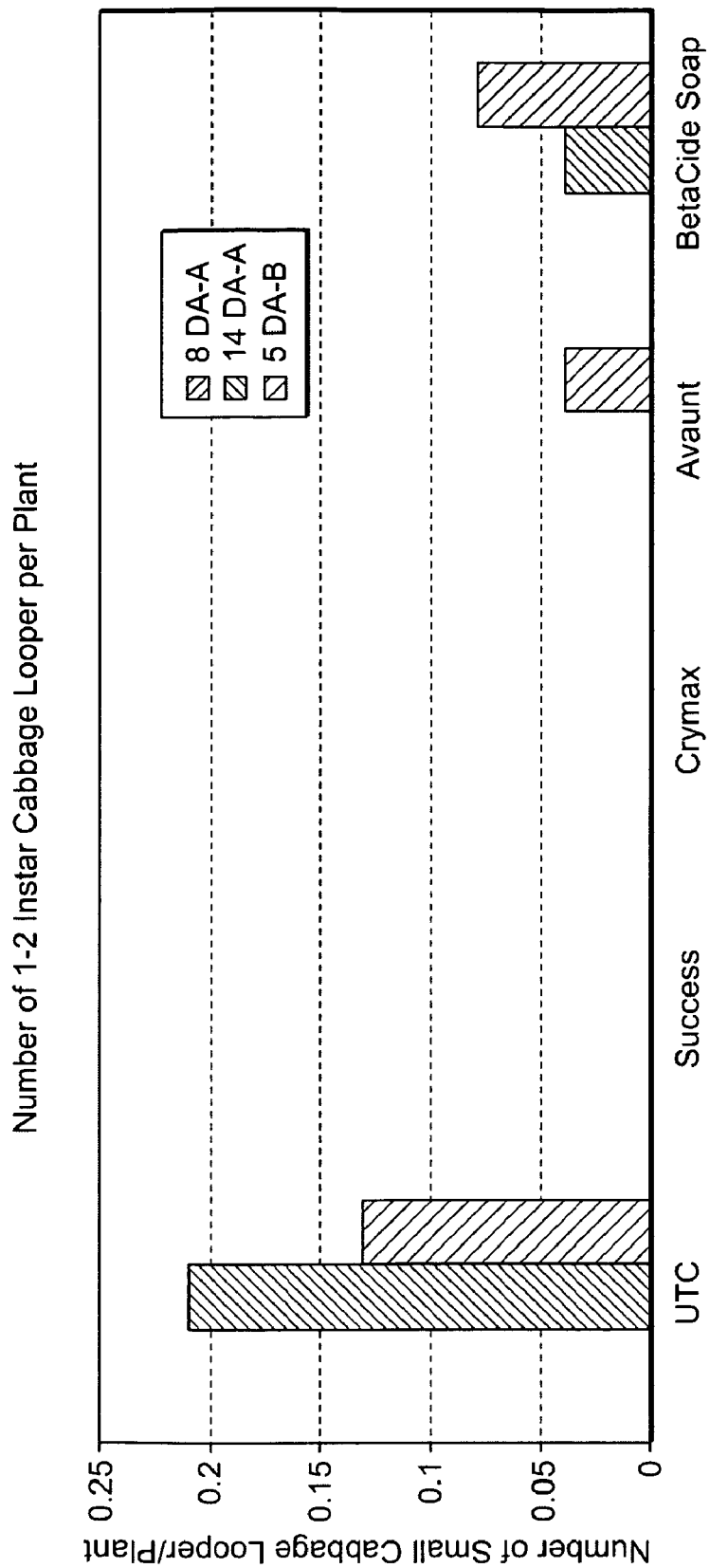
FIG. 11 illustrates the number of $1^{st}$ to $2^{nd}$ instar cabbage loopers per plant.
Figure 12:
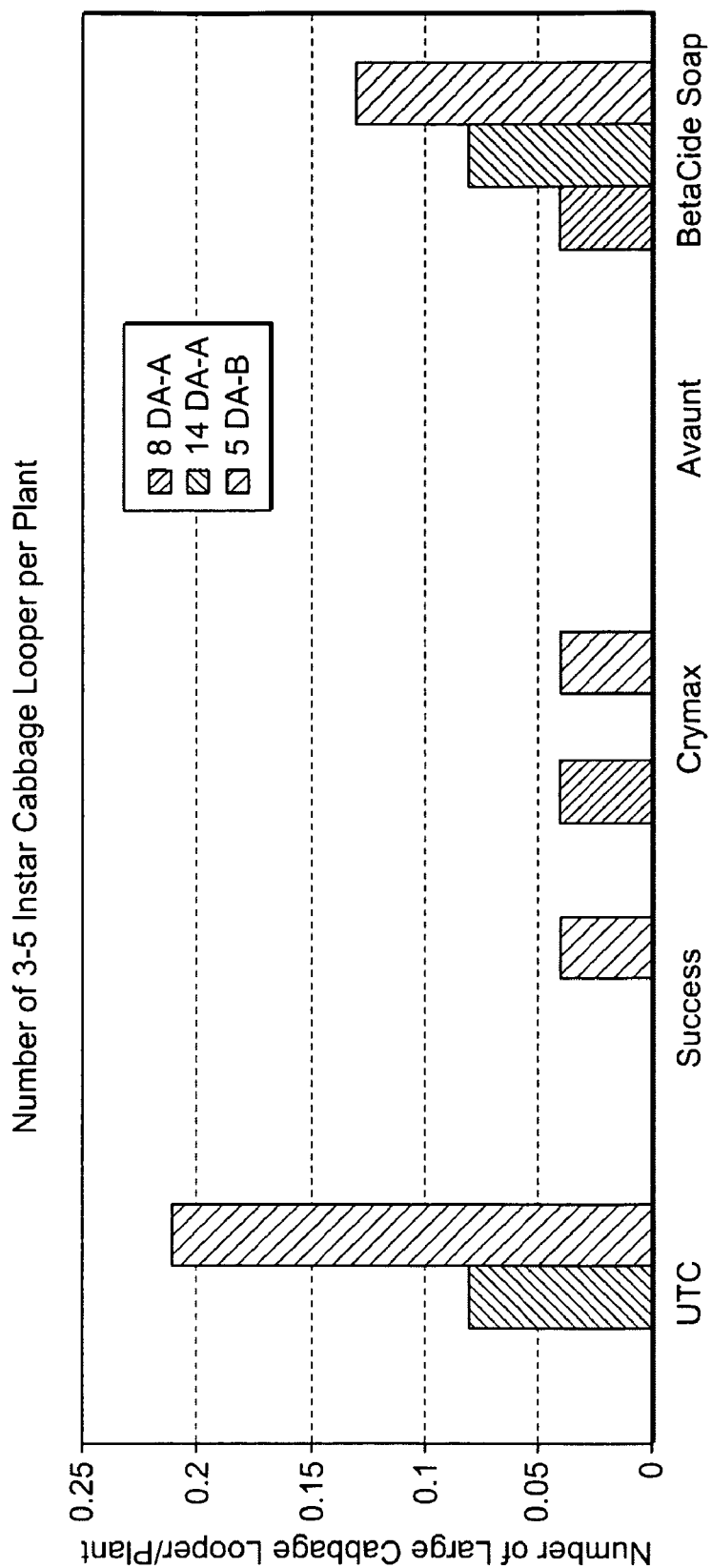
FIG. 12 illustrates the number of $3^{rd}$ to $5^{th}$ instar cabbage loopers per plant.
Figure 13:
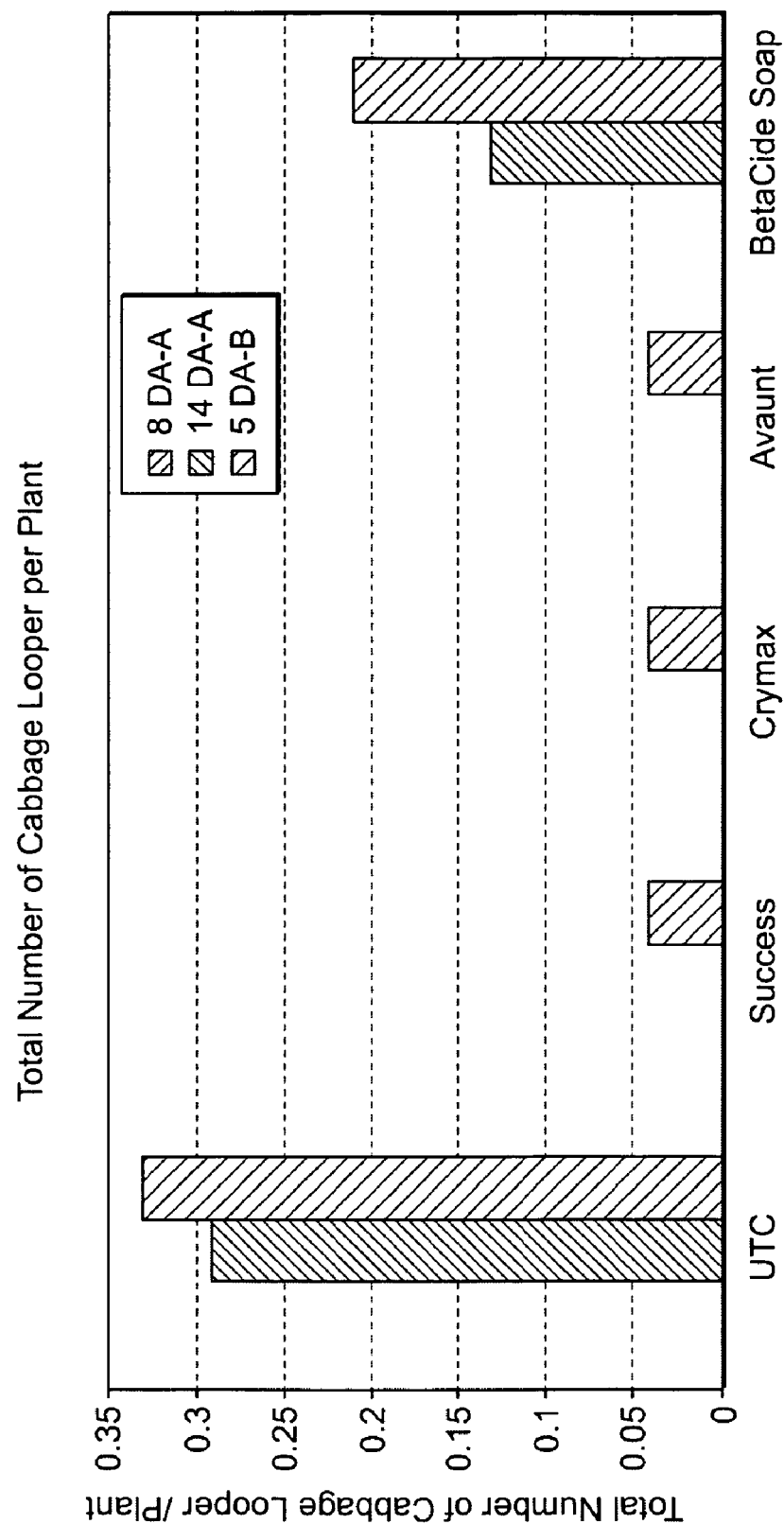
FIG. 13 illustrates the total number cabbage loopers per plant.
Figure 14:
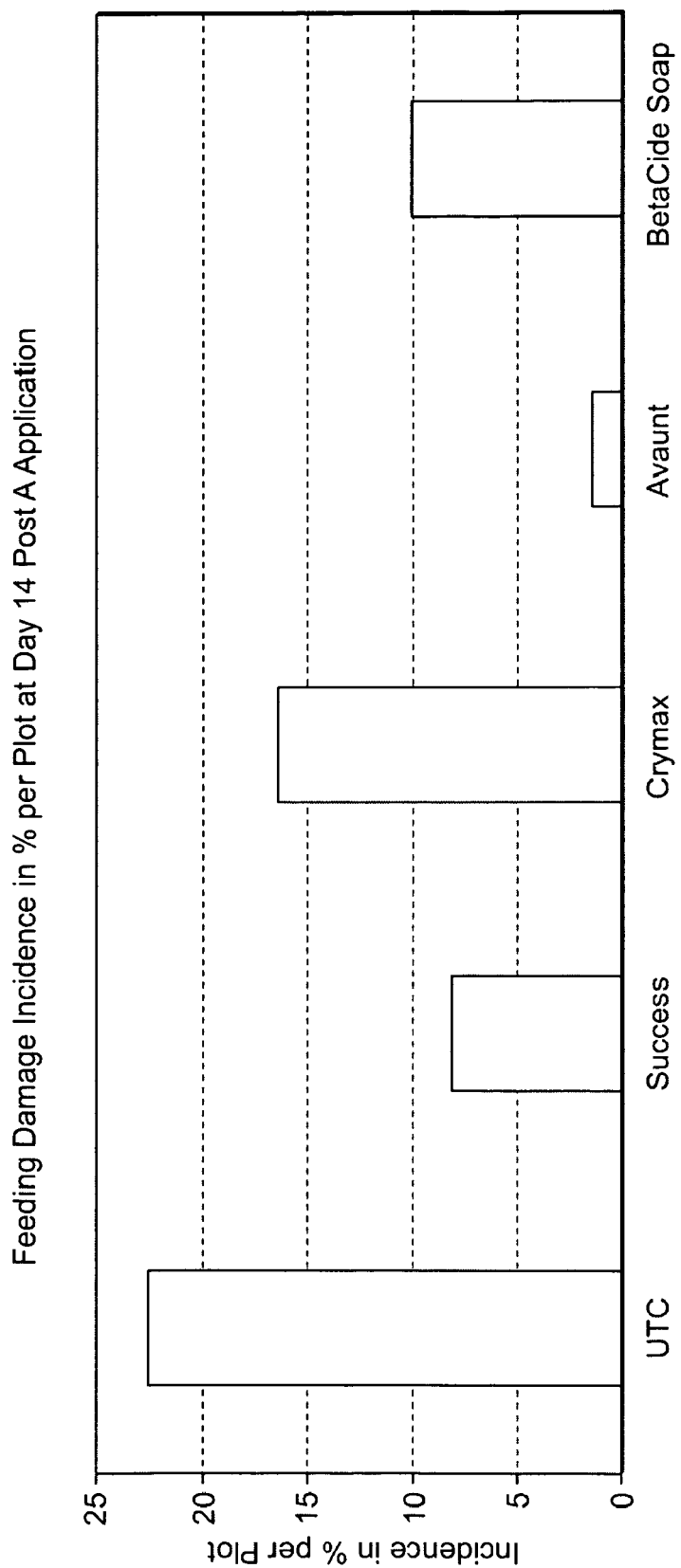
FIG. 14 illustrates the feeding damage from pests in percent per plot.
Figure 15:
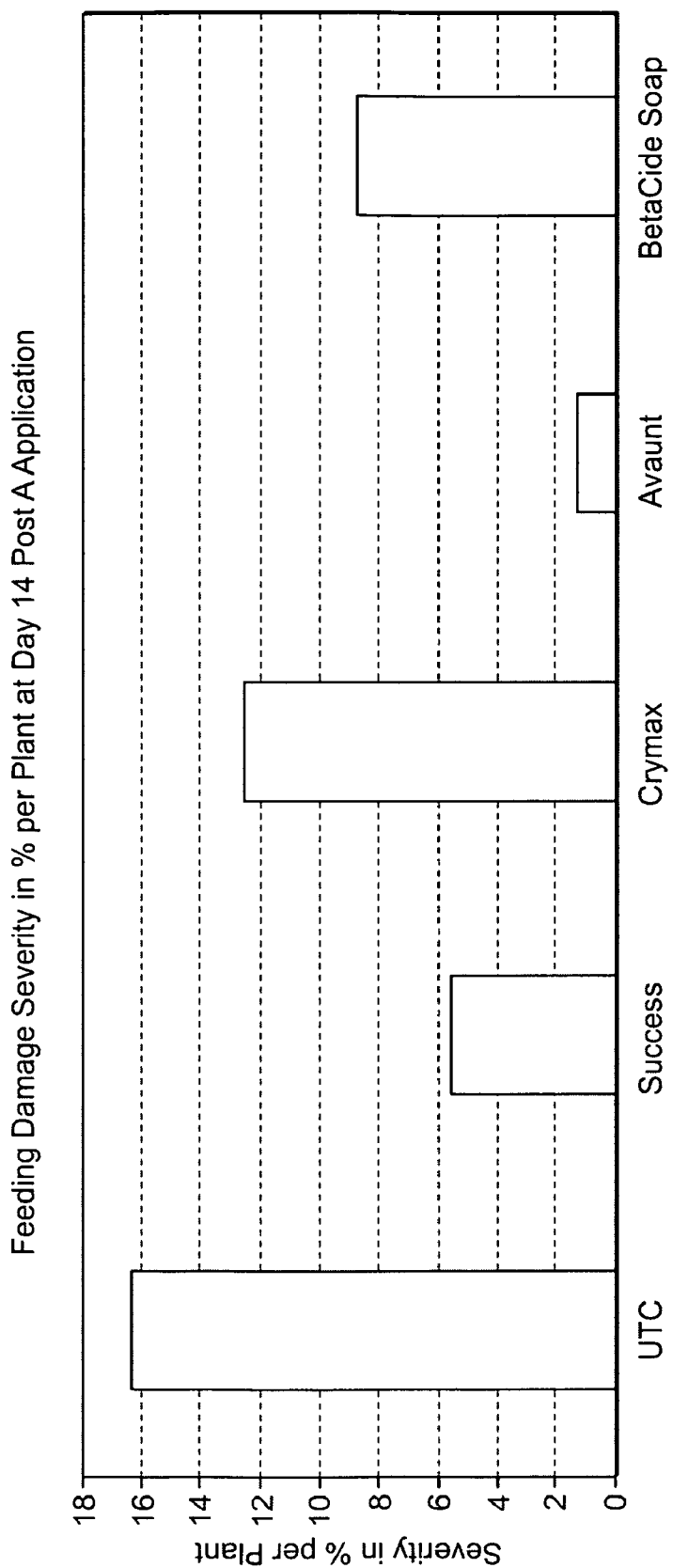
FIG. 15 illustrates the feeding damage severity rated as percent of plant affected.

The percentage of feeding damage on tomato fruit at harvest is shown in Table 6 and FIG. 7. Plants were also evaluated for phytotoxicity in percent.

TABLE 6

Percent Feeding Damage. Feeding damage evaluated in % per plot.

| Trt No. | Treatment Name | Rate | Unit | Feeding Damage in %/Plot Aug. 24, 2005 35 DA-D |
|---|---|---|---|---|
| 1 | UTC | | | 8.5 a |
| 7 | Avaunt | 167 | g/ha | 2.02 b |
| 9 | Success | 208 | ml/ha | 2.83 b |
| 13 | BetaCide | 10 | % v/v | 3.16 b |
| 14 | UTC 2 | | | 9.25 a |

Means followed by same letter do not significantly differ (P = .05, Student-Newman-Keuls); Mean comparisons performed only when AOV Treatment P(F) was significant at mean comparison OSL.

As shown in Table 6 and FIG. 7, BetaCide significantly reduced damage caused by *Lepidoptera* larvae relative to the untreated controls. In fact, Betacide was as effective as the chemical pesticides used. Feeding damage ratings were 8-9% in the untreated plots. Surprisingly, treatment with 10% Betacide reduced feeding damage ratings to just 2-3%. These results indicate that Betacide was effective in controlling *Lepidoptera* pests on agriculturally important crops. No phytotoxicity was observed during these studies.

Example 3

*Lepidoptera* Control on Broccoli

BetaCide was evaluated for the control of several *Lepidoptera* pest species on broccoli in the summer of 2005 in Santa Maria Calif. During this season, larval populations were sporadic. Therefore, foliar evaluations of larval feeding following the application period was used to examine whether Betacide was effective in controlling *Lepidoptera*. Insecticides were applied to each plot two times at 15 day intervals over the course of four weeks. The following formulations were used: Success at 5 fl oz/a; Crymax at 2 lb/a; BetaCide at 10% v/v with Soap at 0.5% v/v; Avaunt at 3.43 oz/a. The soap used was a liquid handsoap (Renown was pink handsoap Deerfield, Ill.). Treatment applications were performed using a $CO_2$ backpack sprayer. The spray boom incorporated six D4 nozzles with #25 spinners and was operated at a pressure of 40-50 psi. Treatments were applied at a dilution of 75 GPA. The boom size was adjusted according to the growth stage of plant to ensure a thorough foliar coverage. Evaluation consisted of identifying and counting *Lepidoptera* pests on six randomly selected plants per plot. The plot dimensions were 3.33'×15'; row spacing was 3.33'; plant spacing was 12". The following pests were identified: Diamondback moth (*Plutella xylostella*), Cabbage Looper (*Trichoplusia ni*) and Imported Cabbage Worm (*Pieris rapae*). Plants were also evaluated for feeding damage incidence on percent per plot. Feeding damage severity was rated as percent per plant affected. Results were compared to an untreated control plot. Results of these studies are shown in Tables 7-14 and FIGS. 8-15.

TABLE 7

Number of Small Diamondback Moth Larvae ($1^{St}$ to $2^{nd}$ Instar per Plant)

| Trt No. | Treatment Name | Rate | Rate Unit | Aug. 30, 2005 −1 DA-A | Sep. 8, 2005 8 DA-A | Sep. 14, 2005 14 DA-A | Sep. 20, 2005 5 DA-B |
|---|---|---|---|---|---|---|---|
| 1 | UTC | | | 0.42 a | 0.13 a | 0.63 a | 0.42 a |
| 2 | Success | 5 | fl oz/a | 0.25 a | 0 a | 0.04 b | 0 b |
|   | Latron B-1956 | 6 | oz/100 gal | | | | |
| 7 | Crymax | 2 | lb/a | 0.37 a | 0.13 a | 0 b | 0.08 b |
|   | Latron B-1956 | 6 | oz/100 gal | | | | |
| 14 | Avaunt | 3.43 | oz/a | 0.04 a | 0 a | 0 b | 0 b |
|   | Latron B-1956 | 6 | oz/100 gal | | | | |
| 16 | BetaCide | 10 | % v/v | 0.08 a | 0 a | 0.21 b | 0.08 b |
|   | Soap | 0.5 | % v/v | | | | |

TABLE 8

Number Large Diamondback Moth Larvae ($3^{rd}$ to $4^{th}$ Instar per plant)

| Trt No. | Treatment Name | Rate | Rate Unit | Aug. 30, 2005 −1 DA-A | Sep. 8, 2005 8 DA-A | Sep. 14, 2005 14 DA-A | Sep. 20, 2005 5 DA-B |
|---|---|---|---|---|---|---|---|
| 1 | UTC | | | 0.06 a | 0 a | 0.29 a | 0.08 a |
| 2 | Success | 5 | fl oz/a | 0.04 a | 0 a | 0 a | 0 a |
|   | Latron B-1956 | 6 | oz/100 gal | | | | |
| 7 | Crymax | 2 | lb/a | 0 a | 0 a | 0.04 a | 0.04 a |
|   | Latron B-1956 | 6 | oz/100 gal | | | | |
| 14 | Avaunt | 3.43 | oz/a | 0 a | 0 a | 0 a | 0 a |
|   | Latron B-1956 | 6 | oz/100 gal | | | | |
| 16 | BetaCide | 10 | % v/v | 0.08 a | 0.04 a | 0.13 a | 0.08 a |
|   | Soap | 0.5 | % v/v | | | | |

TABLE 9

Total Number of Diamondback Moth Larvae per Plant.

| Trt No. | Treatment Name | Rate | Rate Unit | Aug. 30, 2005 −1 DA-A | Sep. 8, 2005 8 DA-A | Sep. 14, 2005 14 DA-A | Sep. 20, 2005 5 DA-B |
|---|---|---|---|---|---|---|---|
| 1 | UTC | | | 0.48 a | 0.13 a | 0.92 a | 0.5 a |
| 2 | Success | 5 | fl oz/a | 0.29 a | 0 a | 0.04 b | 0 b |
|   | Latron B- | 6 | oz/100 gal | | | | |
| 7 | Crymax | | lb/a | 0.37 a | 0.13 a | 0.04 b | 0.13 b |
|   | Latron B- | 6 | oz/100 gal | | | | |
| 14 | Avaunt | 3.43 | oz/a | 0.04 a | 0 a | 0 b | 0 b |
|   | Latron B- | 6 | oz/100 gal | | | | |
| 16 | BetaCide | 10 | % v/v | 0.17 a | 0.04 a | 0.33 b | 0.17 b |
|   | Soap | 0.5 | % v/v | | | | |

TABLE 10

Number of 1-2 Instar Cabbage Looper per Plant

| Trt No. | Treatment Name | Rate | Rate Unit | Sep. 8, 2005 8 DA-A | Sep. 14, 2005 14 DA-A | Sep. 20, 2005 5 DA-B |
|---|---|---|---|---|---|---|
| 1 | UTC | | | 0 a | 0.21 a | 0.13 a |
| 2 | Success | 5 | fl oz/a | 0 a | 0 b | 0 a |
|   | Latron B- | 6 | oz/100 gal | | | |
| 7 | Crymax | 2 | lb/a | 0 a | 0 b | 0 a |
|   | Latron B- | 6 | oz/100 gal | | | |
| 14 | Avaunt | 3.43 | oz/a | 0 a | 0 b | 0.04 a |
|   | Latron B- | 6 | oz/100 gal | | | |
| 16 | BetaCide | 10 | % v/v | 0 a | 0.04 b | 0.08 a |
|   | Soap | 0.5 | % v/v | | | |

TABLE 11

Number of 3-5 Instar Cabbage Looper

| Trt No. | Treatment Name | Rate | Rate Unit | Sep. 8, 2005 8 DA-A | Sep. 14, 2005 14 DA-A | Sep. 20, 2005 5 DA- |
|---|---|---|---|---|---|---|
| 1 | UTC | | | 0 a | 0.08 a | 0.21 a |
| 2 | Success | 5 | fl oz/a | 0 a | 0 a | 0.04 b |
| | Latron B- | 6 | oz/100 gal | | | |
| 7 | Crymax | 2 | lb/a | 0.04 a | 0 a | 0.04 b |
| | Latron B- | 6 | oz/100 gal | | | |
| 14 | Avaunt | 3.43 | oz/a | 0 a | 0 a | 0 b |
| | Latron B- | 6 | oz/100 gal | | | |
| 16 | BetaCide | 10 | % v/v | 0.04 a | 0.08 a | 0.13 ab |
| | Soap | 0.5 | % v/v | | | |

TABLE 12

Total Number of Cabbage Looper per Plant

| Trt No. | Treatment Name | Rate | Rate Unit | Sep. 8, 2005 8 DA-A | Sep. 14, 2005 14 DA-A | 9/20/2 5 DA- |
|---|---|---|---|---|---|---|
| 1 | UTC | | | 0 a | 0.29 a | 0.33 a |
| 2 | Success | 5 | fl oz/a | 0 a | 0 b | 0.04 b |
| | Latron B- | 6 | oz/100 gal | | | |
| 7 | Crymax | 2 | lb/a | 0 a | 0 b | 0.04 b |
| | Latron B- | 6 | oz/100 gal | | | |
| 14 | Avaunt | 3.43 | oz/a | 0 a | 0 b | 0.04 b |
| | Latron B- | 6 | oz/100 gal | | | |
| 16 | BetaCide | 10 | % v/v | 0 a | 0.13 b | 0.21 ab |
| | Soap | 0.5 | % v/v | | | |

TABLE 13

Feeding Damage Incidence in % per Plot

| Trt No. | Treatment Name | Rate | Rate Unit | Sep. 14, 2005 14 DA-A |
|---|---|---|---|---|
| 1 | UTC | | | 22.5 a |
| 2 | Success | 5 | fl oz/a | 8.13 bc |
| | Latron B-1956 | 6 | oz/100 gal | |
| 7 | Crymax | 2 | lb/a | 16.25 ab |
| | Latron B-1956 | 6 | oz/100 gal | |
| 14 | Avaunt | 3.43 | oz/a | 1.25 c |
| | Latron B-1956 | 6 | oz/100 gal | |
| 16 | BetaCide | 10 | % v/v | 10 bc |
| | Soap | 0.5 | % v/v | |

TABLE 14

Feeding Damage Severity in % per Plant Area

| Trt No. | Treatment Name | Rate | Rate Unit | Sep. 14, 2005 14 DA- |
|---|---|---|---|---|
| 1 | UTC | | | 16.25 a |
| 2 | Success | 5 | fl oz/a | 5.63 ab |
| | Latron B-1956 | 6 | oz/100 gal | |
| 7 | Crymax | 2 | lb/a | 12.5 a |
| | Latron B-1956 | 6 | oz/100 gal | |
| 14 | Avaunt | 3.43 | oz/a | 1.25 b |
| | Latron B-1956 | 6 | oz/100 gal | |
| 16 | BetaCide | 10 | % v/v | 8.75 ab |
| | Soap | 0.5 | % v/v | |

These results indicate that BetaCide is better at controlling pests than an alternative pesticide product, which is in widespread use. The BetaCide product gave approximately 50% control of plant damage with the two applications made here, while the *Bacillus* product gave only 23% control during this same period. Standard chemical treatments of Success and Avaunt were 64% and 92% respectively.

Example 4

Control of Insect Damage to Marketable Fruit

Figure 16:
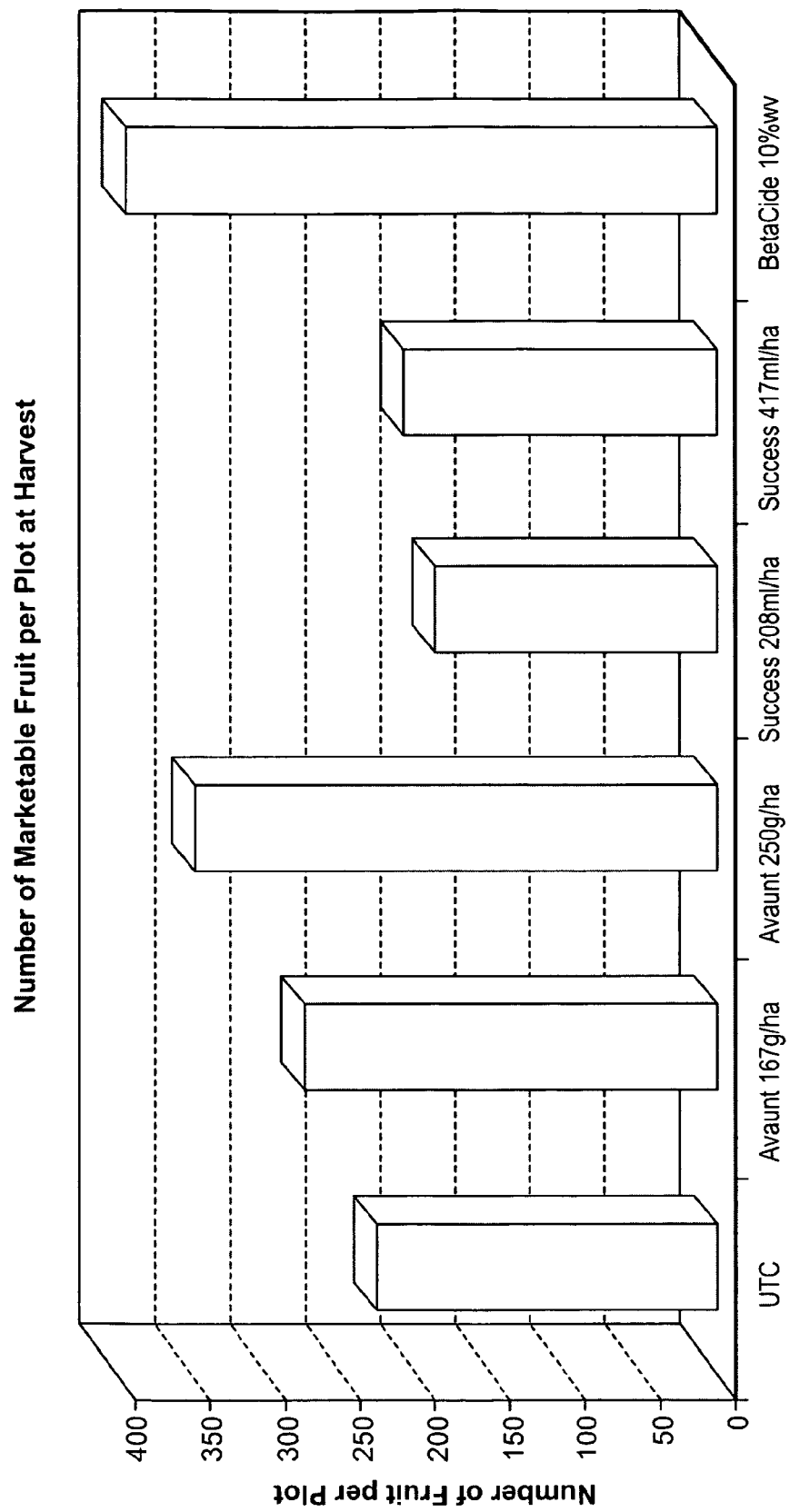
FIG. 16 illustrates the number of marketable fruit per plot at harvest.
Figure 17:
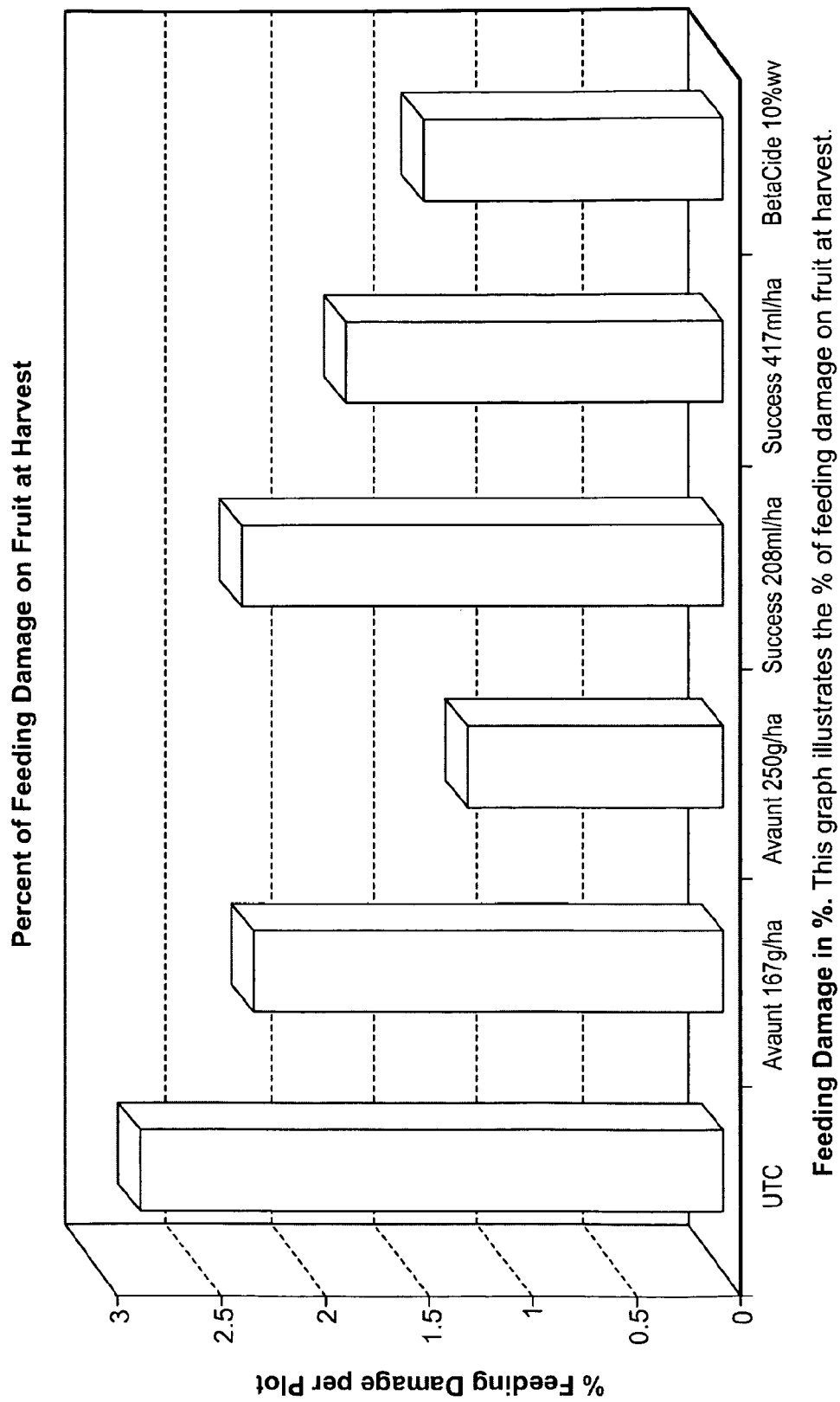
FIG. 17 shows the percent of feeding damage per plot at harvest.

This study was established in the central valley of California near Firebaugh, Calif. in the summer of 2005. The following insecticides were applied 5 times at 7 to 10 day intervals:

BetaCide at 10% v/v; Avaunt at 167 g/ha; Avaunt at 250 g/ha; Success at 208 ml/ha; Success at 417 ml/ha; and an untreated Control. Treatment applications were performed using a $CO_2$ backpack sprayer. The spray boom incorporated six D4 nozzles with #25 spinners and was operated at a pressure of 40 psi. Treatments were applied at a dilution of 80 GPA. The boom size was adjusted according to the growth stage of the plant to ensure a thorough foliar coverage. The boom used is shown in FIG. 1. Plants were evaluated for presence of pests and feeding damage on fruit The results of these studies is shown at Tables 15 and 16. At harvest marketable fruit were counted and feeding damage percent was evaluated (FIGS. 16 and 17).

TABLE 15

Number of Marketable Fruit per Plot at Harvest

| Trt No. | Treatment Name | Rate | Rate Unit | Sep. 2, 2005 49 DA-A |
|---|---|---|---|---|
| 1 | UTC | | | 229.25 bc |
| 7 | Avaunt | 167 | g/ha | 277.5 abc |
| 8 | Avaunt | 250 | g/ha | 349.5 ab |
| 9 | Success | 208 | ml/ha | 189 c |

TABLE 15-continued

Number of Marketable Fruit per Plot at Harvest

| Trt No. | Treatment Name | Rate | Rate Unit | Sep. 2, 2005 49 DA-A |
|---|---|---|---|---|
| 10 | Success | 417 | ml/ha | 211 bc |
| 12 | BetaCide | 10 | % v/v | 395.25 a |

TABLE 16

Percent of Feeding Damage on Fruit at Harvest

| Trt No. | Treatment Name | Rate | Rate Unit | Sep. 2, 2005 49 DA-A |
|---|---|---|---|---|
| 1 | UTC | | | 2.82 a |
| 7 | Avaunt | 167 | g/ha | 2.28 a |
| 8 | Avaunt | 250 | g/ha | 1.24 a |
| 9 | Success | 208 | ml/ha | 2.33 a |
| 10 | Success | 417 | ml/ha | 1.82 a |
| 12 | BetaCide | 10 | % v/v | 1.45 a |

The total feeding damage was less than 3% in untreated plots, which is less than necessary to provide for a statistical analysis of pest control. There was a measurable improvement in marketable yield with BetaCide over the untreated plots and the other treatments in the study.

Example 5

Preparation of Aqueous Hop Acid Compositions

Beta fraction was used to prepare a 10% aqueous beta acids solution. The term "beta fraction" refers to the oily, waxy, resinous portion of a hop extract obtained when the hop extract is washed with caustic water to remove most of the alpha acids. The beta fraction contains mostly beta acids, resins, oils, and waxes. It is also called beta acid oil. The beta fraction may be used, as is, or washed with caustic water to reduce the alpha acids concentration in the beta fraction so that the ratio of alpha acids to beta acids is 0.05, or below, by HPLC analysis. The temperature of the beta fraction was raised to 60° C. with continuous mixing, and caustic was added in the form of KOH to bring the pH to 10-11. Having first determined the beta acids content in the beta fraction by HPLC analysis, a volume of 60° C. water was added, while mixing, so that the beta acids concentration of the aqueous phase was between 10% and 50%. The pH of the solution was adjusted, if necessary, to pH 10-l 11 at 60° C. It was necessary to subtract the volume of KOH added for pH adjustment from the calculated volume of water. Also, a temperature range of 55-70 ° C. was acceptable, although 60° C. was optimal. Mixing was stopped, and the mixture was allowed to sit for at least 45 minutes, during which time the temperature of the solution was maintained at 60° C. The aqueous beta acids phase was then separated from the resinous phase. The aqueous beta acids phase was diluted to a concentration of 10% beta acids as determined by HPLC, while the temperature was maintained at 60° C., and the pH was maintained at 10-11. The aqueous phase was cooled (mixing is optional) to 1-13° C., and allowed to sit for at least 2 hours. The solution was then decanted or filtered.

Small-Scale 10% Aqueous Beta Acids Solution 500 g of beta fraction containing 50% beta acids by HPLC was heated to 60° C. Approximately 250 mL of 20% KOH was added, while stirring with heat to maintain a 60° C. temperature, and to bring the pH up to 10.7. Mixing was stopped, and the mixture was allowed to sit overnight. The following morning, the resinous fraction was set aside and the aqueous fraction was heated to 60° C. and analyzed by HPLC. Water and 20% KOH were added to bring the beta acids concentration to 10%, and the pH to 10.7. The aqueous beta acids solution was refrigerated to 5° C. overnight, and filtered the next morning.

Large-Scale 10% Aqueous Beta Acids Solution Example 1000 kg of beta fraction at 60° C. was placed in a hot water-jacketed tank. Approximately 120 gallons of 20% KOH were added with continuous mixing until the pH of the aqueous phase reached 10.7. The mixing was shut down, but the heat was maintained at 60° C., and the mixture was allowed to sit overnight. The aqueous layer was pumped into a stainless steel, heat-jacketed tank and diluted to a 10% beta acids concentration by HPCL using deionized water. The temperature and pH were maintained at 60° C. and 10.7, respectively. Heating of the tank was stopped, the product was cooled to 10° C., and then allowed to settle overnight. Clouded and precipitated material was pumped to a recycle tank, and the clear beta acids solution was filtered.

Preparation of 10% Aqueous Alpha Acids Solution

Supercritical CO2 extract was used to prepare a 10% aqueous alpha-acids solution. The hop extract was placed in a volume of water calculated to produce an aqueous alpha acids solution, with a concentration of 3-20% by HPLC. An alpha acid concentration of less than 8% was optimum. At this concentration, beta acid solubility in the aqueous phase was lowered. The temperature was raised to 50-70° C., and the pH was adjusted to 6-8, with constant mixing. A pH of 7-8 was optimum. The extract solution was then allowed to sit for at least 45 minutes. The resinous fraction containing beta acids, oils, and waxes was set aside, while the aqueous alpha-acids solution was decanted. The temperature was raised to 60° C. and the pH was raised to 7-9. The solution was analyzed by HPLC. If the alpha-acids concentration was 10% or greater, water was added to bring the concentration to 10%. The solution was cooled to 1-19° C., and filtered or decanted.

If the alpha acids concentration was less than 10%, the aqueous solution was acidified ($H_2SO_4$ or $H_3PO_4$ were satisfactory) at 60° C. to bring the alpha acids out of solution. The alpha acids were washed with fresh 60° C. water and allowed to sit for a minimum of 45 minutes. The water was discarded, and a calculated volume of 60° C. fresh water was added. The volume was calculated to produce a 10% alpha acid concentration by HPLC, also taking into account the volume of caustic necessary for pH adjustment. The alpha acids solution was heated to 60° C., and the pH was raised to 7-9 with KOH solution, as necessary. The aqueous solution was allowed to cool to 1-1 9° C., and filtered or decanted.

Small-Scale 10% Aqueous Alpha Acids Solution Example 800 g of supercritical $CO_2$ extract was added to 2700 mL of deionized water, and the temperature was increased to 60° C., with constant mixing. Approximately 300 mL of 20% KOH was added to bring the pH up to 7.7. The solution was allowed to sit overnight. The resinous fraction containing beta acids, oils, and waxes was set aside, while the aqueous alpha-acids solution was decanted and cooled overnight to 7° C. The aqueous solution was then filtered, while cold, to remove any crystallized beta fraction, and brought back to 60° C. 20% H2SO4 was added with continuous stirring until the pH was 2.5. The resinous alpha acids were separated and washed with fresh 60° C. deionized water. The alpha acids were added to 2000 mL deionized water and brought to 60° C. Approximately 300 mL of 20% KOH were added to bring the pH up to 8.0, and the solution was analyzed by HPLC. Deionized water and 20% KOH were added to bring the concentration and pH up to 10% and 8.9, respectively. The solution was cooled to 5° C. overnight, and filtered.

Creation of Emulsions from 10% Aqueous Beta Acids and Alpha Acids Solutions

10% aqueous beta acids solutions and 10% aqueous alpha acids solutions are clear with no precipitated material. They are similar to weak iced tea in color, clarity, and consistency. Dilutions of these 10% solutions with tap or well water result in the formation of stable aqueous emulsions which have the appearance of pineapple juice and do not exhibit any separation even after days of storage. They are very stable, and precipitate does not form even down to a dilution of 1:16. Also, as these solutions are diluted with water, pH drops by about 0.5 pH units but not enough to cause precipitation.

Other Embodiments

From the foregoing description, it will be apparent that variations and modifications may be made to the invention described herein to adopt it to various usages and conditions. Such embodiments are also within the scope of the following claims.

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

All patents and publications mentioned in this specification are herein incorporated by reference to the same extent as if each independent patent and publication was specifically and individually indicated to be incorporated by reference.

What is claimed is:

1. A method of controlling a fungus, the method comprising contacting a fungus or spore selected from the group consisting of *Botrytis, Erysiphe, Leveillula, Sphaerotheca, Rasutoria, Microsphaera, Podosphaera, Peronospora, Phytophthora, Pseudoperonospora,* and *Plasmopara* with an effective amount of a composition comprising an isolated hop derivative, thereby controlling the fungus.

2. The method of claim 1, wherein the *Botrytis* is *Botrytis cinerea, Botrytis paeoniae* or *Botrytis tulipae*.

* * * * *

UNITED STATES PATENT AND TRADEMARK OFFICE
CERTIFICATE OF CORRECTION

| | | |
|---|---|---|
| PATENT NO. | : 8,142,820 B2 | Page 1 of 1 |
| APPLICATION NO. | : 12/311259 | |
| DATED | : March 27, 2012 | |
| INVENTOR(S) | : Gene Probasco | |

It is certified that error appears in the above-identified patent and that said Letters Patent is hereby corrected as shown below:

On the Title page:

Item (73) Assignee: should read:

~~John L. Hass, Inc., Washington, DC (US)~~ John I. Haas, Inc., Washington, DC (US)

Signed and Sealed this
Twenty-fourth Day of July, 2012

David J. Kappos
*Director of the United States Patent and Trademark Office*